United States Patent
Oostman, Jr. et al.

(10) Patent No.: US 8,512,356 B2
(45) Date of Patent: Aug. 20, 2013

(54) FOLLICULAR UNIT HARVESTING TOOLS INCLUDING DEVICES AND THEIR USE FOR SEVERING CONNECTIVE TISSUE

(75) Inventors: Clifford A. Oostman, Jr., Hansville, WA (US); Miguel G. Canales, Los Altos, CA (US)

(73) Assignee: Restoration Robotics, Inc., San Jose, CA (US)

( * ) Notice: Subject to any disclaimer, the term of this patent is extended or adjusted under 35 U.S.C. 154(b) by 185 days.

(21) Appl. No.: 12/134,165

(22) Filed: Jun. 5, 2008

(65) Prior Publication Data

US 2009/0005765 A1 Jan. 1, 2009

Related U.S. Application Data

(60) Provisional application No. 60/946,236, filed on Jun. 26, 2007.

(51) Int. Cl.
*A61B 17/50* (2006.01)
*A61B 17/34* (2006.01)

(52) U.S. Cl.
USPC .......................................... 606/133; 606/185

(58) Field of Classification Search
USPC .................... 606/51, 106, 107, 108, 110, 127, 606/133, 181, 184, 185, 187, 205, 209, 210, 606/211; 600/585–587, 564–567
See application file for complete search history.

(56) References Cited

U.S. PATENT DOCUMENTS

| | | | |
|---|---|---|---|
| 1,433,340 A | 10/1922 | Clark | |
| 4,393,872 A * | 7/1983 | Reznik et al. | 600/565 |
| 4,682,606 A * | 7/1987 | DeCaprio | 600/567 |
| 4,716,901 A | 1/1988 | Jackson et al. | |
| 5,464,405 A * | 11/1995 | Fujitsu et al. | 606/51 |
| 5,573,008 A | 11/1996 | Robinson et al. | |
| 5,578,054 A | 11/1996 | Arnold | |
| 5,584,841 A | 12/1996 | Rassman | |
| 5,788,651 A | 8/1998 | Weilandt | |
| 5,843,000 A * | 12/1998 | Nishioka et al. | 600/566 |
| 5,885,226 A | 3/1999 | Rubinstein et al. | |

(Continued)

FOREIGN PATENT DOCUMENTS

| | | |
|---|---|---|
| GB | 1505264 | 3/1978 |
| WO | 97/06749 | 2/1997 |
| WO | 02/07602 | 1/2002 |

OTHER PUBLICATIONS

James A. Harris. "New Methodology and Instrumentation for Follicular Unit Extraction: Lower Follicle Transection Rates and Expanded Patient Candidacy". Dermatol Surg. 32: 1: Jan. 2006.

(Continued)

*Primary Examiner* — Kathleen Holwerda
*Assistant Examiner* — Sarah W Aleman
(74) *Attorney, Agent, or Firm* — Lena I Vinitskaya; Sharon Upham; Guy Cumberbatch

(57) ABSTRACT

Devices and methods are disclosed which provide for harvesting hair follicular units, including severing any remaining connective tissue strands during the harvesting process, so that the harvested follicular units are retained in the harvesting tool without being damaged. The devices and methods of the present invention are especially useful with the partially or substantially automated systems and methods for hair harvesting and transplantation. The follicular unit harvesting tools may comprise a harvesting cannula and a grasping device moveable relative to each other.

42 Claims, 16 Drawing Sheets

(56) References Cited

U.S. PATENT DOCUMENTS

| | | | |
|---|---|---|---|
| 5,893,853 A | 4/1999 | Arnold | |
| 5,972,021 A | 10/1999 | Huttner et al. | |
| 6,027,512 A | 2/2000 | Bridges | |
| 6,080,175 A | 6/2000 | Hogendijk | |
| 6,110,127 A * | 8/2000 | Suzuki | 600/565 |
| 6,142,957 A * | 11/2000 | Diamond et al. | 600/567 |
| 6,228,084 B1 * | 5/2001 | Kirwan, Jr. | 606/52 |
| 6,248,081 B1 * | 6/2001 | Nishtalas et al. | 600/567 |
| 6,471,709 B1 | 10/2002 | Fawzi et al. | |
| 6,572,625 B1 | 6/2003 | Rassman | |
| 6,585,746 B2 | 7/2003 | Gildenberg | |
| 6,616,683 B1 | 9/2003 | Toth et al. | |
| 6,770,026 B2 * | 8/2004 | Kan et al. | 600/114 |
| 6,918,880 B2 * | 7/2005 | Brookner et al. | 600/565 |
| 6,939,318 B2 | 9/2005 | Stenzel | |
| 7,172,604 B2 | 2/2007 | Cole | |
| 2005/0267506 A1 | 12/2005 | Harris | |
| 2007/0078466 A1 | 4/2007 | Bodduluri et al. | |
| 2007/0078473 A1 * | 4/2007 | Bodduluri et al. | 606/167 |
| 2007/0078475 A1 | 4/2007 | Bodduluri et al. | |
| 2007/0123800 A1 | 5/2007 | Nishtala et al. | |
| 2008/0234602 A1 | 9/2008 | Oostman et al. | |
| 2009/0240261 A1 | 9/2009 | Drews et al. | |
| 2010/0082042 A1 | 4/2010 | Drews | |

OTHER PUBLICATIONS

Inaba, M. and Inaba, Y., "Androgenetic Alopecia, Modern Concepts of Pathogenesis and Treatment", 29. Operative Treatment for Androgenetic Alopecia, Springer, 1996, pp. 238-244, 309. (9 pages).

PCT Int'l Search Report and Written Opinion in connection with corresponding Patent Application No. PCT/US2008/065987, Applicant: Restoration Robotics, Inc. Forms PCT/ISA/237, dated Jan. 14, 2010. (5 pages).

"New Instrumentation for Three-Step Follicular Unit Extraction". Robert M. Bernstein and William R. Rassman. Hair Transplant Forum International (Official publication of the International Society of Hair Restoration Surgery). vol. 16, No. 1, Jan. /Feb. 2006. (4 pages).

PCT International Search Report and Written Opinion of PCT/US2008/065987, Applicant Restoration Robotics, Inc., Forms PCT/ISA/210, 220 and 237, dated Oct. 7, 2008 (10 pages).

* cited by examiner

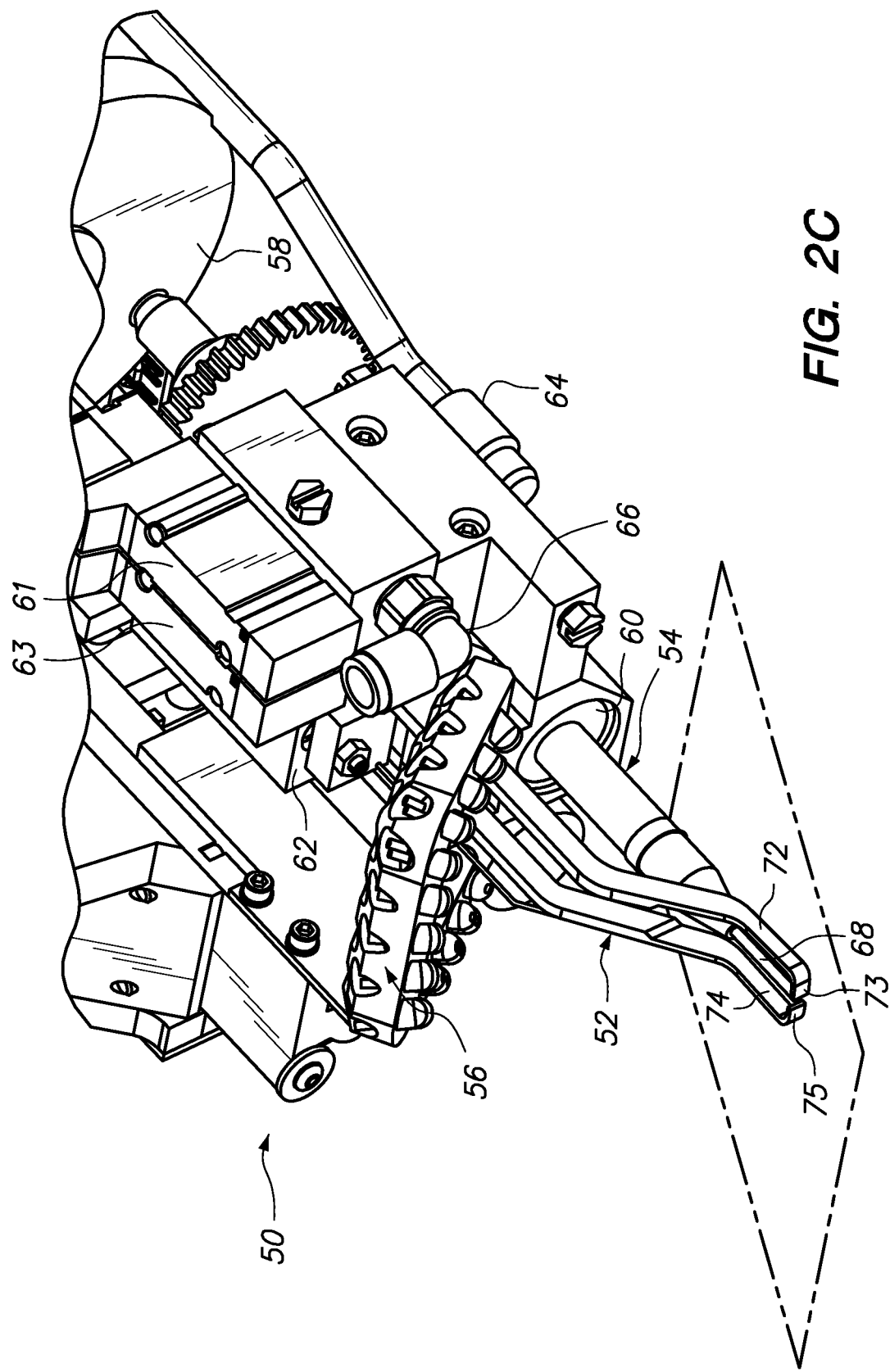

FOLLICULAR UNIT HARVESTING TOOLS INCLUDING DEVICES AND THEIR USE FOR SEVERING CONNECTIVE TISSUE

CROSS-REFERENCE TO RELATED APPLICATIONS

The present application claims the benefit under 35 U.S.C. §119 to U.S. Provisional Application No. 60/946,236, filed on Jun. 26, 2007, the contents of which are incorporated herein by reference as though set forth in full.

FIELD OF INVENTION

This invention relates generally to devices and methods used for the harvesting and/or transplantation of hair follicles and follicular units, and more particularly to devices and methods for effectively severing follicular units from connective tissue during the harvesting process.

BACKGROUND

Hair transplantation procedures are well-known, and typically involve harvesting donor hair grafts, for example, from the side and back fringe areas of the patient's scalp ("donor areas"), and implanting the harvested grafts in a bald area ("recipient area"). Historically, the harvested hair grafts were relatively large (3-5 mm), although more recently the donor grafts may be single "follicular units," which are naturally occurring aggregates of 1-3 (and much less commonly, 4-5) closely spaced hair follicles that are distributed randomly over the surface of the scalp. In one well-known process, a linear portion of the scalp is removed from a donor area by dissection, using a scalpel to cut down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods may also be used.

In "Androgenetic Alopecia" (Springer 1996), M. Inaba & Y. Inaba disclose and describe a method for harvesting singular follicular units by positioning a hollow punch needle having a cutting edge and interior lumen with a diameter of 1 mm, which is about equal to the diameter of critical anatomical parts of a typical follicular unit. The needle punch is axially aligned with an axis of a follicular unit to be extracted and then advanced into the scalp to cut the scalp about the circumference of the selected follicular unit. Thereafter, the follicular units are easily removed, e.g., using forceps, for subsequent implantation into a recipient site with a specially devised insertion needle.

U.S. Pat. No. 6,585,746 (Gildenberg) discloses using a robotic system for hair transplantation, the system including a robotic arm and a hair follicle introducer associated with the robotic arm. U.S. Patent Publications 2007/0078466 and 2007/0078475, which are each assigned to Restoration Robotics, Inc., of Mountain View, Calif. (assignee of the present application), also disclose automated (e.g., robotic) systems used for transplanting hair follicular units, including a multi-part tool assembly carried on a robotic arm. The tool assembly is independently controllable relative to the robotic arm, and includes an inner, "harvesting" cannula with a longitudinal axis that is automatically aligned (under image-guidance) with a selected follicular unit to be harvested from a donor area of a body surface, and then advanced relative to the body surface so that an open, tissue coring distal end of the harvesting cannula penetrates the body surface surrounding the selected follicular unit to a depth sufficient to substantially encapsulate the follicular unit. The harvesting cannula is then withdrawn from the body surface with the follicular unit engaged by and retained in an interior lumen thereof. An outer, "implanting" cannula is disposed coaxially over (and moveable relative to) the harvesting cannula, wherein a tissue piercing distal end of the implanting cannula is used to puncture a recipient area of the body surface and form an implantation cavity, with the follicular unit displaced from the harvesting cannula lumen into the implantation cavity.

Some manual and partially automated devices for hair harvesting and transplantation that are known in the art include, for example, the use of a vacuum source to assist in extracting hair follicles from a body surface. However, it has been determined that during the harvesting procedure, the vacuum source may not always provide enough "grasping" force to fully extract the follicular unit from the body surface. For example, tissue strands may sometimes tether the follicular unit to the scalp as the follicular unit is being retracted from the scalp, and can end up pulling the follicular unit out of the harvesting cannula, even against the force of the vacuum source. In addition, the pulling force of the tissue strands may damage the follicular unit, even if it breaks free from the scalp.

SUMMARY OF THE INVENTION

Devices and methods are disclosed and described which provide for harvesting hair follicular units, including cleanly severing any remaining connective tissue strands during the harvesting process, so that the harvested follicular units are retained in the harvesting cannula without any substantial damage. More particularly, various embodiments of follicular unit harvesting apparatus utilizing one or more grasping devices for grasping the harvested follicular units upon retraction from the body surface are disclosed and describe herein. In various embodiments, the grasping device extends just distally beyond the distal end of the harvesting cannula, and grasps (and in some embodiments severs or causes to be severed, or both grasps and severs) any remaining connective tissue attached to the harvested follicular unit as the harvesting cannula exits the skin surface with the harvested follicular unit contained therein. In various embodiments, the grasping device may comprise a pair of opposing arms, each arm having a tip which moves into contact with (or very close proximity to) the other tip when the grasping device is in the closed position. Some embodiments simply clamp the strands of tissue and sever the tissue by pulling force, while other embodiments having cutting tips which cut the strands.

In one embodiment, a follicular unit harvesting tool includes a harvesting cannula having an interior lumen sized for harvesting follicular units, and an open, tissue-coring distal end in communication with the lumen. The harvesting tool further includes a grasping device having a pair of opposing arms, each arm extending to a respective tip, wherein one or both of the harvesting cannula and grasping device being movable relative to the other. The grasping device has an open position, in which the arm tips are separated, and a closed position, in which the arm tips are positioned in close proximity to each other and beyond the distal end of the harvesting cannula to facilitate grasping and/or severing of a connective tissue strand connecting a follicular unit to a body surface from which the follicular unit was harvested. An actuation system is operatively coupled to the grasping device and is configured to provide controlled, synchronized movement of the grasping device arms from the open position to the closed position, and from the closed position to the open position, respectively. Alternatively, the actuation system may be configured to provide controlled lateral and longitudinal movement of the grasping device arms, wherein lateral movement of the grasping device arms is controlled independently from longitudinal movement of the grasping device arms.

More particularly, in various embodiments, the grasping device arm tips comprise respective opposing tissue engaging surfaces. In one embodiment, the respective tissue engaging surfaces are serrated surfaces that mate when the grasping device is in the closed position. In another embodiment, the respective tissue engaging surfaces define a center-hole when the grasping device is in the closed position, the center-hole being sized to accommodate a portion, for example, a bulb of a follicular unit extending from the lumen of the harvesting cannula.

In some embodiments, one or both grasping device arm tips comprise a tissue cutting surface. By way of non-limiting example, the respective grasping device arm tips may be beveled and configured to overlap and cut the connective tissue strand as the grasping device is moved from the open position to the closed position. By way of another, non-limiting example, the grasping device arm tips may have respective tissue cutting surfaces configured to overlap and cut the connective tissue strand in a scissor-like action as the grasping device is moved from the open position to the closed position. By way of a still further, non-limiting example, one of the grasping device arm tips comprises a tissue cutting surface, and the other comprises a dull surface configured to meet the tissue cutting surface when the grasping device is in the closed position to facilitate cutting of the tissue strand.

In some embodiments, at least one of the grasping device arm tips forms or is otherwise coupled to an energy transmitting element configured to sever the connective tissue strand. By way of non-limiting examples, the energy transmitting element may be an electrode, an ultrasound transducer, or a laser, for conveying radio frequency, mechanical wave, or optical energy, respectively, through the connective tissue strand to sever same. In one such embodiment, one of the grasping device arm tips comprises a first electrode, and the other comprises a second electrode, the first and second electrodes configured for completing a radio frequency energy circuit through the connective tissue strand to thereby sever same.

In various embodiments, a fluid conduit is coupled to one of the grasping device arms, the fluid conduit having an outlet positioned for delivering fluid (e.g., saline) proximate the open distal end of the harvesting cannula. In some embodiments, respective fluid delivery conduits are coupled to both arms, each having an outlet configured to deliver fluid (e.g., saline) proximate the open distal end of the harvesting cannula. The presence of the fluid may have several beneficial effects, including but not limited to flushing away excess tissue and blood around the area of the harvested follicular unit on the body surface, providing moisture to the follicular unit, lubricating a pathway of the follicular unit from the harvesting cannula opening to a storage location, and helping to seal the distal end opening of the harvesting cannula surrounding the harvested follicular unit to thereby increase the pulling force exerted on the follicular unit of a vacuum source in communication with the interior harvesting cannula lumen.

In some embodiments, the respective tissue engaging surfaces of the grasping device arm tips having corresponding grooves formed therein, which define a cavity for receiving a distal end portion of the harvesting cannula when the grasping device is in the closed position. In one such embodiment, outer sides of the respective grasping device arm tips are tapered to their respective distal ends so as to form an arrow-shape when the grasping device is in the closed position, and wherein the grasping device arms are moveable relative to the harvesting cannula so that the respective distal ends of the grasper arm tips may be inserted into the body surface to a depth beyond an insertion depth of the distal end of the harvesting cannula while harvesting of a follicular unit, and so that the respective tissue engaging surfaces of the grasping device arm tips can be moved together into the closed position to retain the harvested follicular unit within the harvesting cannula as the respective harvesting cannula and grasping device are moved out of the body surface. A respective fluid conduit may be coupled to one or both of the grasping device arms and having respective outlets located in an inner wall of the respective tissue engaging surface grooves for delivering fluid into the cavity when the grasping device is in the closed position. The cavity may be dimensioned to at least partially seal the enclosed open distal end portion of the harvesting cannula within the cavity when the grasping device is in the closed position to thereby enhance a pulling force of a vacuum source in communication with the harvesting cannula lumen. Optionally, a further tissue grasping device may be provided, wherein at least one of the second tissue grasping device arm tips has an energy transmitting element (e.g., an RF electrode, ultrasound transducer, or laser) configured to sever the connective tissue strand while the first tissue grasping device is in the closed position. By way of non-limiting example, in one such embodiment, one of the second grasping device arm tips comprises a first electrode, and the other comprises a second electrode, the first and second electrodes configured for completing a radio frequency energy circuit through the connective tissue strand to thereby sever same.

In some embodiments, the follicular unit harvesting tool further comprises a guide member having an axial passageway through which the harvesting cannula extends. The guide member has a distal interior bore in communication with the axial passageway, and a distal facing end configured to mate with the grasping device arm tips when the grasping device is in the closed position so as to at least partially seal the interior bore and thereby enhance a pulling force of a vacuum source in communication with the harvesting cannula lumen when the distal end of the harvesting cannula is positioned in the interior bore of the guide member. In one such embodiment, the guide member axial passageway has an inner diameter sufficiently close to an outer diameter of the harvesting cannula so that tissue extending outwardly from the cannula distal end is displaced inwardly as the cannula distal end is withdrawn from the interior bore into the axial passageway of the guide member. In a same or different embodiment, the distal facing end of the guide member configured to dislodge from the grasper arm tips any tissue extending from a follicular unit carried in the harvesting cannula as the grasper device is moved from the closed position to the open position while initially mated to the guide member.

According to another aspect of the invention, in one embodiment, a method for harvesting follicular units from a body surface includes inserting a distal end of a harvesting tool into the body surface to surround and core a follicular unit; withdrawing the distal end of the harvesting tool from the body surface with the follicular unit at least partially retained in an interior lumen of the harvesting tool; and moving one or both of a grasping device operatively associated with the harvesting tool and the harvesting tool relative to each other so that two arm tips of a pair of opposing arms of the grasping device extend beyond the distal end of the harvesting tool and in close proximity to each other to facilitate grasping and/or severing of a connective tissue strand connecting the follicular unit to the body surface.

The method of this embodiment may further comprise severing the connective tissue strand connecting the follicular unit to the body surface. In one such embodiment, the method includes applying energy to the connective tissue strand through an energy transmitting element operatively connected to at least one arm of the grasping device to sever the connective tissue strand from the follicular unit. By way of non-limiting example, one of the grasping device arms may have a tissue engaging tip comprising a first electrode, and the other tissue engaging tip comprising a second electrode, wherein the connective tissue strand is severed by completing a radio frequency energy circuit through the strand via the respective electrodes.

In one embodiment, the grasping device comprises a first tissue grasping device, and the method includes engaging the follicular unit and the connective tissue strand with the first tissue grasping device, and delivering energy to sever the connective tissue strand via an energy transmitting element operatively connected to at least one arm of a second tissues grasping device.

In yet another embodiment, the arms of the grasping device have corresponding grooves to define a cavity, and the method includes moving the harvesting tool and/or the grasping device relative to each other such that the distal end of the harvesting tool is received within the cavity. Preferably, the cavity is dimensioned to at least partially seal the enclosed open distal end portion of the harvesting tool, for example, a cannula, within the cavity to thereby enhance a pulling force of a vacuum source in communication with the harvesting cannula lumen. In one such embodiment, the method includes moving the grasping device relative to the harvesting cannula to thereby insert the respective arm tips of the grasping device into the body surface to a depth beyond an insertion depth of the distal end of the harvesting tool, and closing tissue engaging surfaces of the grasping device arm tips to retain the harvested follicular unit within the harvesting tool as the harvesting tool is retracted from the body surface.

According to yet another aspect of the present invention, in one embodiment, a method for harvesting follicular units from a body surface includes positioning an open, tissue-coring distal end of a harvesting cannula proximate a follicular unit to be harvested; inserting the harvesting cannula distal end into the body surface, surrounding and thereby coring the follicular unit; withdrawing the harvesting cannula distal end from the body surface with the follicular unit at least partially retained in an interior lumen of the harvesting cannula; closing opposing tissue engaging surfaces of a grasping device operatively associated with the harvesting cannula to thereby engage one or both of (i) a portion of the follicular unit extending out of the open distal end of the cannula, and (ii) a connective tissue strand connecting the follicular unit to the body surface; and severing the connective tissue strand by retracting the grasping device from the body surface.

Various embodiments of the disclosed follicular harvesting methods may further include delivering fluid (such as saline) through a fluid conduit coupled to the grasping device, the fluid conduit having an outlet positioned for delivering fluid proximate the distal end of the harvesting tool. The fluid may provide several benefits, including (without limitation) flushing away excess tissue and blood around the area of the harvested follicular unit on the body surface, providing moisture to the follicular unit, lubricating a pathway of the follicular unit within the harvesting cannula, and helping to seal the distal end of the harvesting cannula surrounding a harvested follicular unit to increase the pulling force of a vacuum source in communication with the interior harvesting cannula lumen.

BRIEF DESCRIPTION OF THE DRAWINGS

The foregoing and other aspects of various embodiments of the present invention will best be appreciated with reference to the detailed description of embodiments in conjunction with the accompanying drawings, wherein:

FIGS. 2A-2C are perspective views of an exemplary embodiment of a follicular unit harvesting tool incorporating one embodiment of a grasping device.

DETAILED DESCRIPTION OF THE ILLUSTRATED EMBODIMENTS

In the following Detailed Description, reference is made to the accompanying drawings that show by way of illustration some exemplary embodiments in which the invention may be practiced. In this regard, directional terminology, such as "top," "bottom," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized, and that many structural or logical changes may be made to the illustrated embodiments, without departing from the scope of the present invention. It is to be further understood that the various features of the illustrated embodiments may be used with or incorporated into further embodiments, even if not so illustrated or specifically described.

The term "harvesting tool" as used herein refers to any number of tools or end effectors that are capable of removing or harvesting follicular units from a body surface. In this sense, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The terms "coupled," or "attached," or "mounted" as used herein, may mean directly or indirectly coupled, attached, or mounted through one or more intervening components. The distal end of the harvesting cannula may have many different forms and configurations (e.g., beveled, sharp, dull, textured, have slotted openings or side windows, etc), as may be desired for accessing the body surface, coring and retaining the harvested follicular unit. By way of non-limiting example, the harvesting cannula may include a pair of coaxially positioned cannulas, including a first one with a tissue piercing distal tip used to make the initial incision into the body surface, and a second one having a dull tip used to core the follicular unit after the initial incision is made. Examples of such a harvesting tool are disclosed in U.S. Patent Publication 2005/0267506 to Harris.

In order to better understand the context and uses of the illustrated and described embodiments of the invention, an exemplary (automated) hair transplantation system is first described for purposes of illustration and not limitation. It is to be understood that various embodiments of the invention may be used with this exemplary automated system, as well as with many other types of follicular unit harvesting systems and apparatus, including automated, semi-automated, and manually operated systems and instruments.

Figure 1:
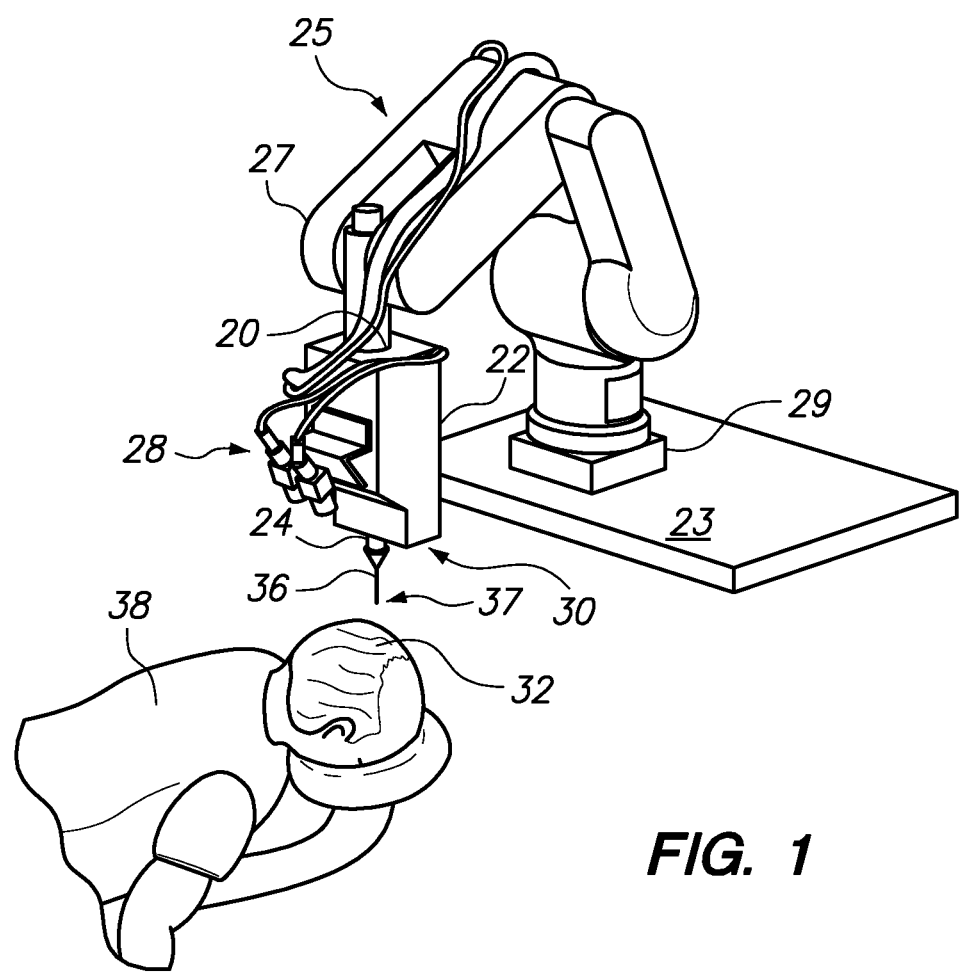
FIG. 1 is a perspective view of a robotic arm system used for positioning and orienting a follicular unit harvesting cannula extending from a tool assembly housing carried by a robotic arm and used for harvesting human hair follicular units.

FIG. 1 depicts an exemplary image-guided robotics system 25, as described in detail in the above-referenced U.S. Patent Publications 2007/0078466 and 2007/0078475. The robotics system 25 includes a robotic arm 27 having a follicular unit harvesting tool assembly 30 attached to a distal tool plate 20 of the robotic arm 27. The harvesting tool assembly 30 includes a harvesting needle (or "cannula") 36 extending from a tubular body 24, which in turn extends from a tool housing 22 attached to the tool plate 20. The harvesting cannula 36 is axially stiff, e.g., made of a hard metal or plastic, and thin-walled to facilitate tissue penetration. The cannula 36 has an open, tissue-coring (e.g., rough or serrated) distal tip 37 in communication with an interior lumen appropriately sized for harvesting singular human hair follicular units by coring the respective follicular units and extracting them from a body surface (typically but not necessarily a scalp). By way of non-limiting examples, embodiments of the harvesting cannula 36 may have interior lumens that range from approximately 0.3 millimeters to 2.0 millimeters in diameter. In one embodiment, the harvesting cannula lumen has a diameter that is approximately 1 millimeter in diameter. Notably, different sized harvesting cannulas 36 may be used for harvesting single-follicle follicular units than for harvesting multi-follicle follicular units. In either case, an inner wall surface of the harvesting cannula lumen may be textured to facilitate frictional grasping the respective follicular units for extraction from the body surface after they are cored.

The robotic arm 27 has a base 29 mounted on a stable platform (table) 23. A patient 38 is positioned relative to the robotic arm 27, so that a targeted body surface (in this instance, the donor area on the back of a patient's scalp) 32 is directly underlying the distal tip 37 of the harvesting cannula 36. As is described in the above-referenced U.S. Patent Publications 2007/0078466 and 2007/0078475, the robotic system 25 includes one or more cameras 28 (two are visible in FIG. 1) mounted on the tool housing 22. A processor (not shown) associated with the robotic system 25 receives and processes images acquired by the one or more cameras 28. The processor and/or a controller (also not shown) that is operatively associated with the processor are configured to precisely maneuver the arm 27 in six degrees of freedom based, at least in part, on images acquired by the one or more cameras 28 and processed by the processor. In this manner, the robotic arm 27 automatically and precisely positions the harvesting cannula 36 at desired locations, and in desired orientations relative to follicular units targeted for harvesting from the body surface (e.g., the donor region on the scalp 32 of the patient 38 shown in FIG. 1) based on control signals derived at least in part from image data acquired by the one or more cameras 28. Movement of the harvesting cannula 36 relative to the patient 38 may be provided by a number of different mechanical, electro-mechanical, pneumatic, hydraulic, magnetic, and other known systems and mechanisms located in the tool housing 22 and coupled for effecting controlled movement of the harvesting cannula 36 in addition to (and synchronized with) the controlled movement of the robotic arm 27.

In particular, for harvesting a follicular unit from a body surface (e.g., scalp 32), the robotic arm 27 positions and aligns the harvesting cannula 36 with a longitudinal axis of a selected follicular unit to be harvested. The harvesting cannula 36 is then advanced over the selected follicular unit by motion of the robotic arm 27 and/or a separate drive assembly located in the tool housing 22 that provides independently controlled axial translation of the harvesting cannula 36, preferably accompanied by simultaneous rotational movement of the harvesting cannula about its longitudinal axis (e.g., by a servo motor located in the housing 22), with the open distal end 37 of the cannula 36 penetrating the body surface into the subcutaneous fatty layer surrounding and underlying the targeted follicular unit. The harvesting cannula 36 is then withdrawn from the body surface by motion of the robotic arm 27 and/or drive assembly within the tool housing 22 to thereby extract the follicular unit from the body surface.

It should be appreciated that, in alternate embodiments, the harvesting tool assembly may be hand-held and positioned, in which case movement of the harvesting cannula relative to the body surface may be manual, semi-automated, or completely automated. The harvesting cannula may be fixed or independently moveable relative to the remainder of the tool assembly, whether the tool assembly is hand-held or attached to a moveable arm (e.g., robotic arm 27 in FIG. 1). In embodiments in which the tool assembly is carried on a robotic arm, movement of the harvesting cannula relative to the body surface may be performed by movement of the arm relative to the body surface, movement of the harvesting cannula relative to the robotic arm, or a combination of each. Similarly, in hand-held embodiments, movement of the harvesting cannula relative to the body surface may be performed by movement of the operator's arm relative to the body surface, movement of the harvesting cannula relative to the tool assembly, or a combination of each.

In some embodiments, whether automated, semi-automated, or entirely manual, the harvesting cannula may be rotated about its longitudinal axis as it penetrates the body surface to enhance its tissue-coring effectiveness. In some or all embodiments, the wall of the harvesting cannula lumen may be textured in order to facilitate grasping and extracting the follicular unit. In some or all embodiments, a vacuum source may be selectively placed in communication with the harvesting cannula lumen to apply a proximally directed "pulling" force to facilitate grasping and extracting the follicular units. These features may also be helpful in retaining the follicular unit in the harvesting cannula lumen after it is harvested.

It should be appreciated that the particular configuration and arrangement of the harvesting cannula is not critical to implementing the invention. For example, instead of a single harvesting cannula, the harvesting tool (whether automated, semi-automated, or manual) may employ axially-aligned, dual harvesting cannulas used for a sequential, two-step harvesting motion, such as described in the above-referenced U.S. Patent Publication 2005/0267506. Also, the tool assembly may include a separate implanting cannula that may be co-axially arranged with the harvesting cannula, as is taught in the above-referenced U.S. Patent Publications 2007/0078466 and 2007/0078475. Still further harvesting cannula embodiments are possible, such as (without limitation) a "two-part" harvesting and implanting cannula as shown and described in commonly assigned U.S. patent application Ser. No. 12/049,170, filed Mar. 14, 2008; Publication Number to be added after publication.

In some cases, as a follicular unit is retracted from a body surface (e.g., a donor region on the back of a scalp) within the harvesting cannula, some tissue strands may tether the follicular unit to the body surface. As a result, as the harvesting cannula is retracted out and away from the body surface, these tissue strands may pull the follicular unit out of the harvesting cannula, or the pulling force of the tissue strands may damage the follicular unit. Even where a vacuum and/or textured interior surface of the harvesting cannula is utilized, the forces may not be sufficient to break these tissue strands as the harvesting cannula is retracted and/or as the follicular unit is moved proximally into the harvesting cannula lumen. In accordance with the present invention, in order to cleanly separate the harvested follicular unit from such tissue strands, and maintain the follicular unit within the harvesting cannula without causing any significant damage thereto, a grasping device may be incorporated with the harvesting cannula utilized to help sever any remaining strands of tissue connecting the follicular unit to the body surface as it is harvested. In various embodiments, the grasping device is a mechanism that grasps and severs the strands of tissue by one or both of a pinching of the strand(s) by the grasper proximate the follicular unit base and the pulling force of the retracting harvesting cannula while the harvested follicular unit is secured in place by the (closed) grasper. Additionally and/or alternatively, the grasping device may employ a passive or active cutting mechanism (e.g., a mechanical blade, a laser, an ultrasonic energy device, or an electrode for conducting RF energy) to cut the strands of tissue from the harvested follicular unit.

Figure 2A:
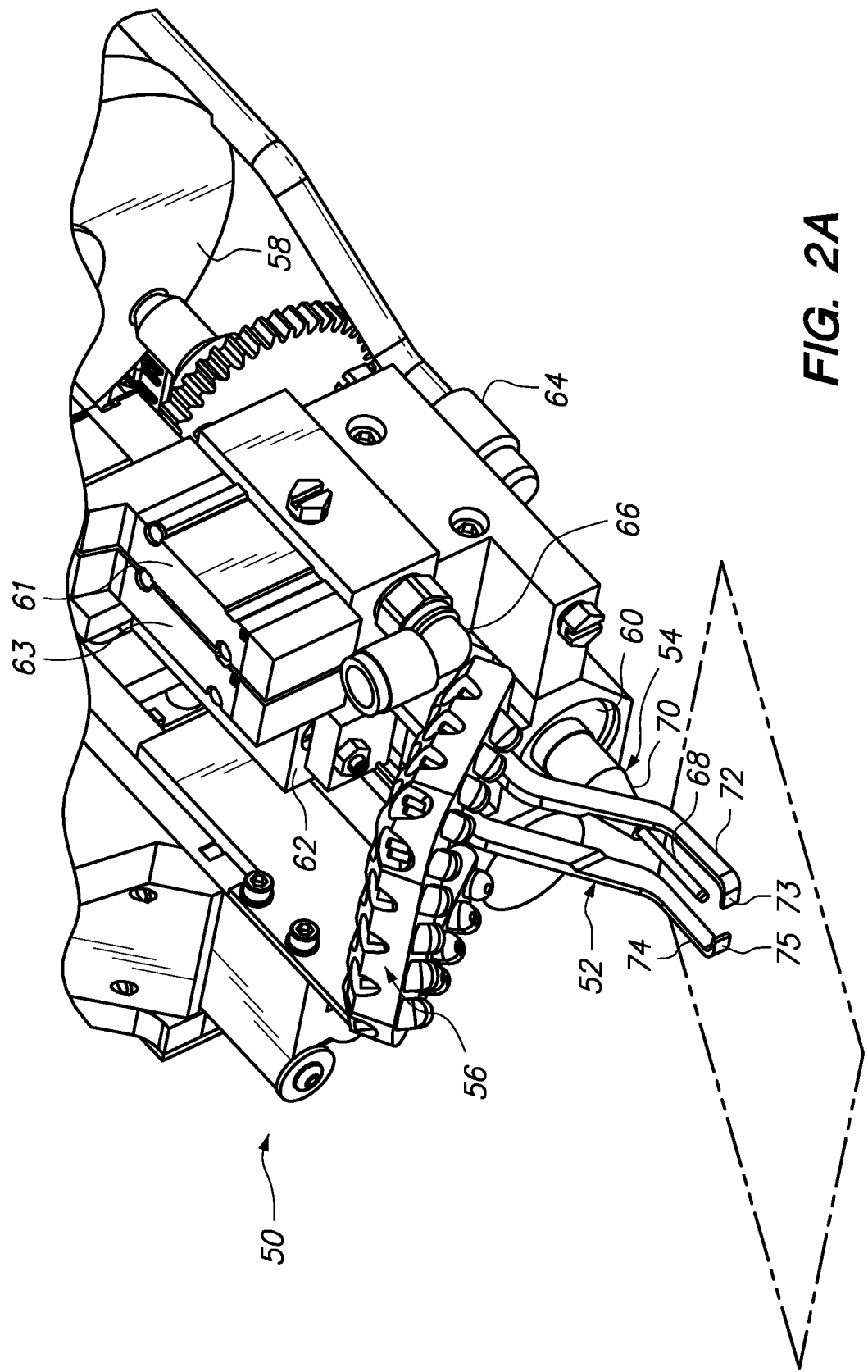
Figure 2B:
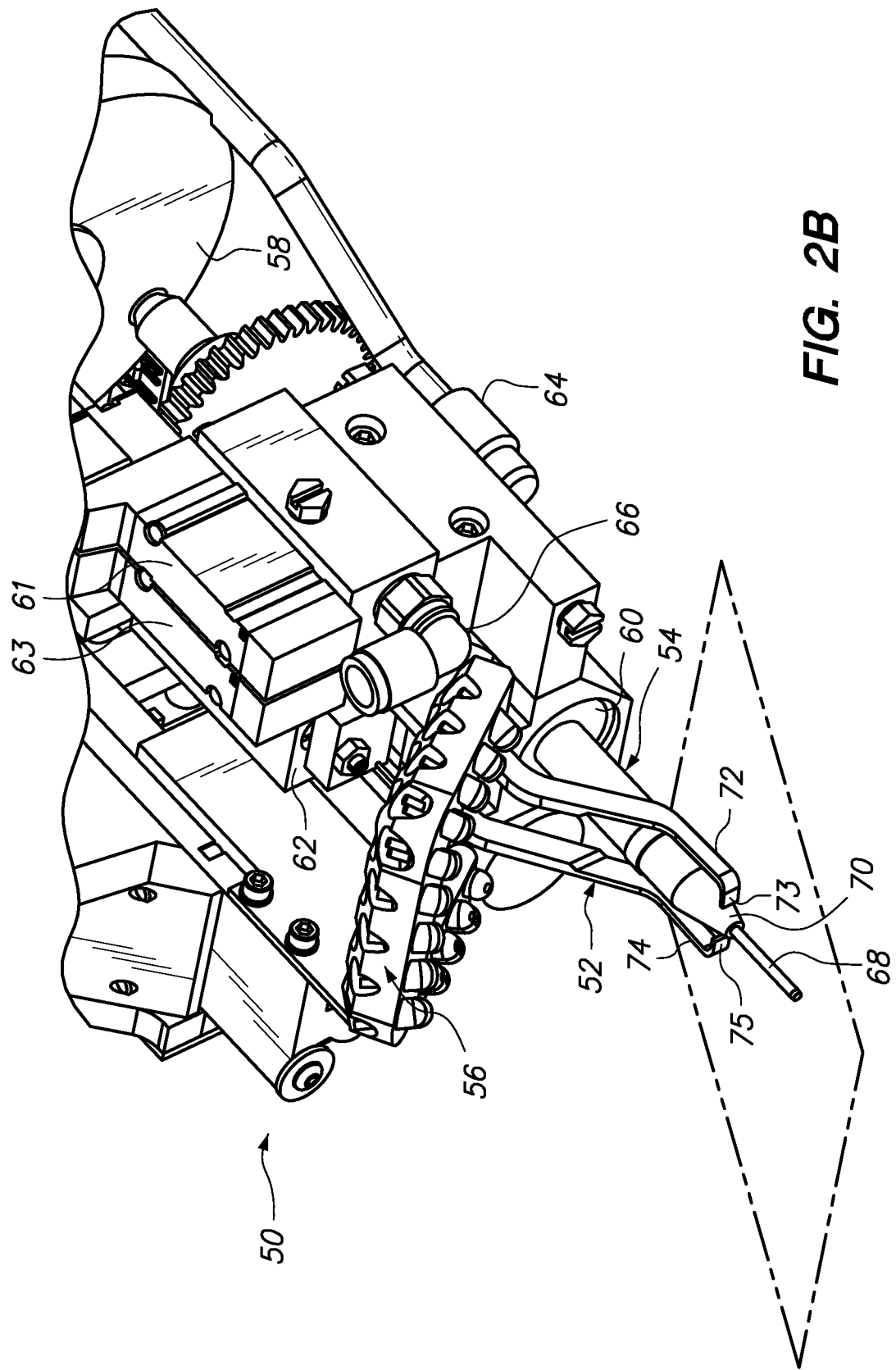

An exemplary embodiment of a follicular unit harvesting system 50 including one such grasping device 52 is depicted in FIGS. 2A-2C. The system 50 may comprise components utilized in the harvesting tool assemblies described in the above-referenced U.S. Patent Publications 2007/0078466 and 2007/0078475, including various modifications which will be readily apparent to those skilled in the art. In addition to the grasping device 52, the system 50 may generally comprise a harvesting tool assembly 54, an LED illumination assembly 56, and a storage cartridge 58 for storing harvested follicular units for later implantation.

The respective grasping device 52 and the harvesting tool assembly 54 are pneumatically actuated in this exemplary embodiment, but it should be understood that other actuation devices may be utilized, such as electric motors, solenoids, etc. Accordingly, the harvesting tool assembly 54 is operatively coupled to a first air cylinder 60, which is in fluid communication with a first pneumatic actuation valve 61; and the grasping device 52 is operatively coupled to a second air cylinder 62, which is in fluid communication with a second pneumatic actuation valve 63. A source of compressed air 64 is in fluid communication with the respective first and second pneumatic actuation valves 61 and 63, as well as an air exhaust vent 66. The harvesting tool assembly 54 comprises a harvesting cannula 68 extending from a hub 70 coupled to the first air cylinder 60. The grasping device 52 has a pair of arms 72 and 74, which extend proximally from respective distal tips 73 and 75 to actuating cams 78 and 80 (see FIG. 3) operatively coupled to the second air cylinder 62.

Turning to FIG. 3A, the actuating cams 78 and 80 each comprise a base (82 and 84, respectively) having a cam slot (86 and 88, respectively) and slider pin hole (87 and 89, respectively). The respective slider pin holes 87 and 89 receive a slider pin 90 which is coupled to a slider 92. A stationary "cam pin" 94 is received by the respective cam slots 86 and 88 of the actuating cams 78 and 80. The slider 92 is operatively coupled to an air cylinder rod 96, which is in turn received in the second air cylinder 62.

Figure 3:
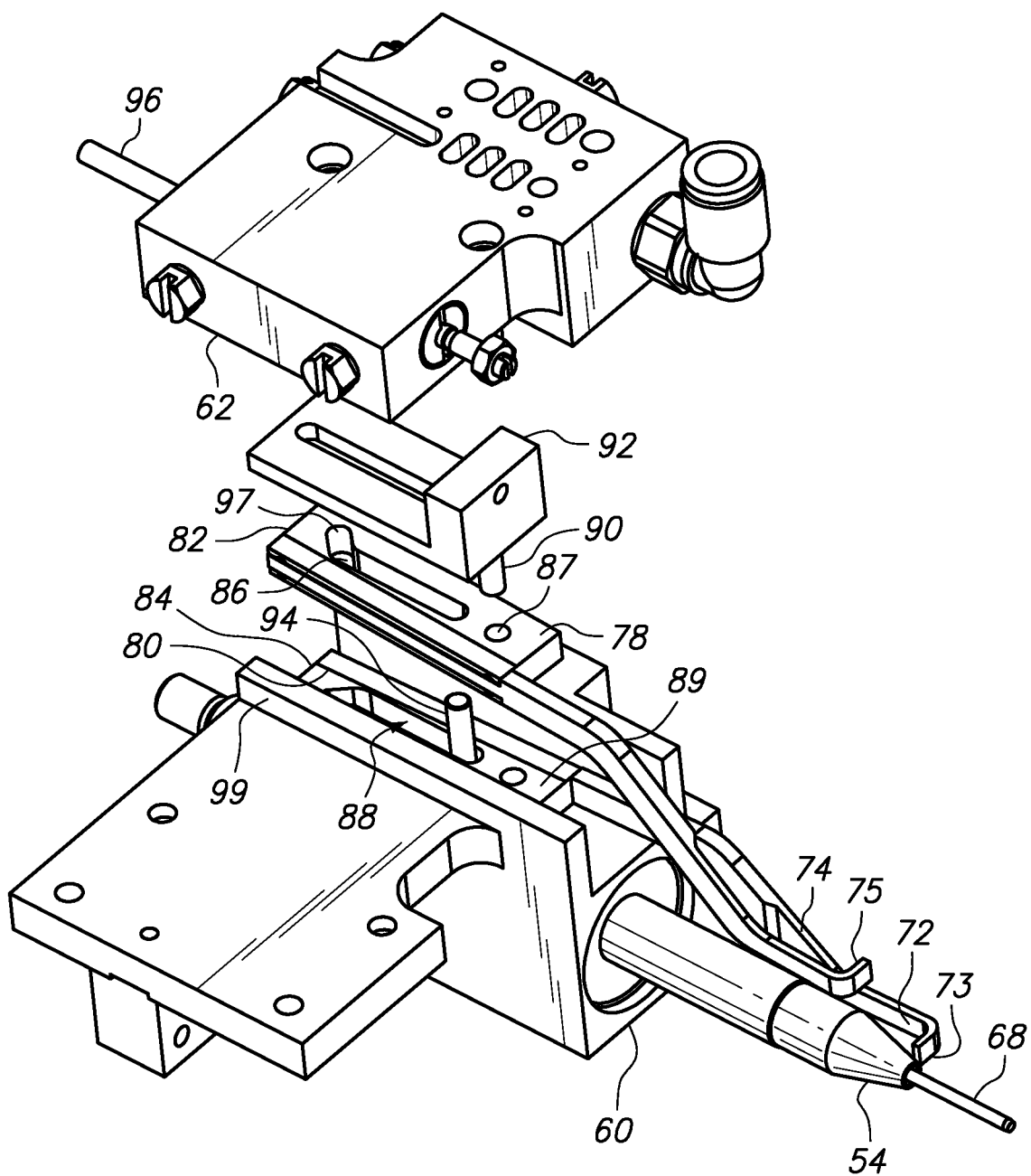
FIG. 3 is a perspective, exploded view of a first pneumatic actuation system used for actuating the respective grasping device and harvesting cannula of the harvesting tool shown in FIGS. 2A-2C.

Operation of this exemplary cam system is as follows: The air cylinder rod 96 is actuated by operation of the second pneumatic actuation valve 63, which pressurizes the second air cylinder 62, and causes the slider 92 to move distally if the grasping device arms 72 and 74 are being closed, or proximally if the arms 72 and 74 are being opened. The motion of the slider 92 and (by extension) the slider pin 90 causes the actuating cams 78 and 80 to move along with the slider 92, thereby moving the respective tips 73 and 75 of the grasping device arms 72 and 74 in a respective distal or proximal direction, depending on the particular step of the harvesting operation. And, as the actuating cams 78 and 80 move distally or proximally, the cam slots 86 and 88 move relative to the cam pin 94. When respective angled portions 97 and 99 of the respective cam slots 86 and 88 travel along the cam pin 94, the cams 78 and 80 rotate about the slider pin 90, thereby causing the respective arms 72, 74 and tips 73 and 75 to move towards each other in a clamping motion when the cams 78 and 80 move distally, or away from each other in a releasing motion when the cams 78 and 80 move proximally. Preferably, the cams 78 and 80 are positioned so that the respective grasper arms 72 and 74 move symmetrically about the centerline of the harvesting cannula 68. In this manner, the cam system shown in FIG. 3 provides controlled, synchronized movement of the grasping device arms 72 and 74 from the open position to the closed position, and from the closed position to the open position, respectively.

An alternative cam system may be employed, which is configured to provide controlled lateral and longitudinal movement of the grasping device arms 72 and 74, wherein lateral movement of the arms is controlled independently from longitudinal movement, thus allowing the grasping device arms close after they have been extended longitudinally. In particular, the air cylinder rod 96, may extend the grasping device arms 72 and 74 forward to the tip of the harvesting needle, 68. Once the grasping device arms 72 and 74 are fully extended to the tip of the harvesting needle, 68, a secondary air cylinder may be employed to push-pull the grasping arms 72 and 74 toward each other, much like the manner in which a hand-caliper on a bicycle push-pulls the brake calipers together. A compression spring between the grasping device arms 72 and 74 may separate the device arms when the secondary air cylinder is released, thereby allowing the grasping device arms to retract longitudinally. Many and various other appropriate mechanisms for providing controlled movement of the grasping device arms in one or both of the lateral and longitudinal directions are also contemplated and within the scope of the present invention.

Figure 5A:
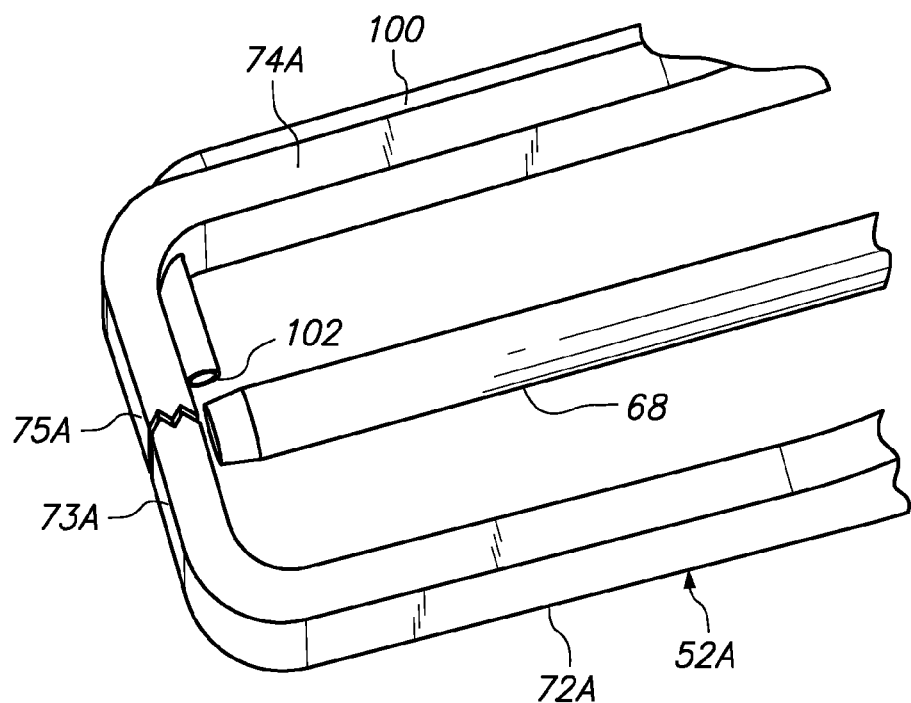
FIGS. 5A-5G are respective perspective views of alternative exemplary embodiments of the grasping device for use with the harvesting tool shown in FIGS. 2A-2C.
Figure 5B:
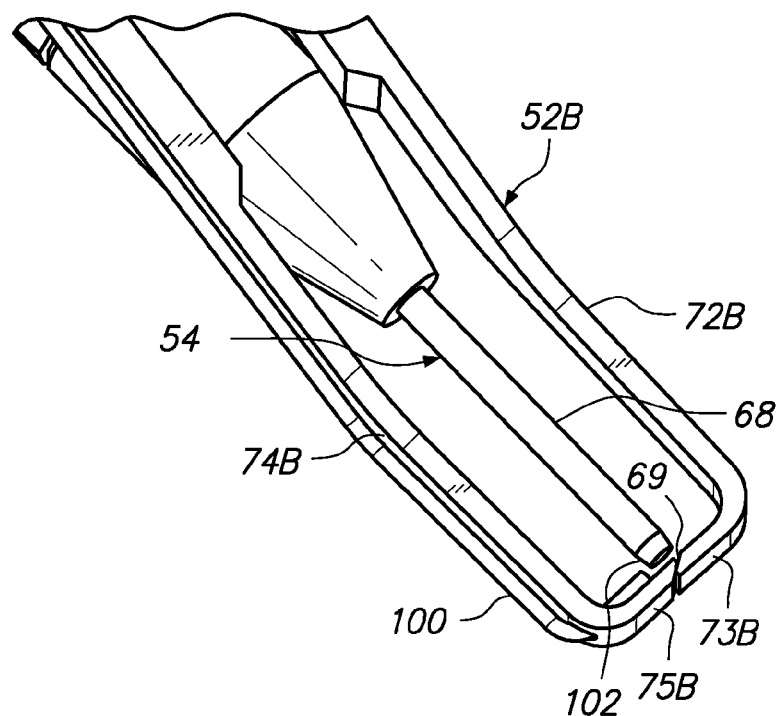

As best seen in FIGS. 5A and 5B, a fluid delivery tube 100 may also be provided with the harvesting apparatus, the tube 100 extends along one of the arms (arm 74B in the illustrated embodiment of FIG. 5B) of the grasping device 52B (described in greater detail below). The fluid delivery tube 100 has an outlet 102 located near the distal end opening 69 of the harvesting cannula 68 when the grasping device 52B is in a closed (or "clamping") position (also shown in FIG. 2C). The fluid delivery tube 100 is used to introduce a fluid, such as saline, into the harvesting cannula 68 and surrounding area, as the harvesting cannula is retracted from the body surface carrying a newly harvested follicular unit. The fluid provides several benefits, including flushing away excess tissue and blood around the area of the harvested follicular unit on the body surface, providing moisture to the follicular unit, lubricating a pathway of the follicular unit from the harvesting cannula opening to the storage cartridge 58, and helping to seal the distal end 69 of the harvesting cannula 68 surrounding the harvested follicular unit to thereby increase the pulling force exerted on the follicular unit of a vacuum source in communication with the interior harvesting cannula lumen.

FIG. 2A depicts the harvesting tool assembly 54 and grasping device 52 in a "harvest ready" position, in which the grasping device 52 is in an open position with the grasper arm tips 73 and 75 spread apart and extended beyond the distal end of the harvesting cannula 68. To harvest a follicular unit, the system 50 aligns the harvesting cannula 68 with a selected follicular unit to be harvested, for example, in a same manner or very similar to that described above for the system 25. The harvesting cannula 68 is then may be advanced over the selected follicular unit by actuation of the first air cylinder 60, which same forward motion advances the harvesting cannula 68 distally beyond the respective arm tips 73 and 75 of the grasping device 52 for puncturing the skin and surrounds the follicular unit (not shown). This "harvesting position" configuration of the respective harvesting tool assembly 54 and grasping device 52 is shown in FIG. 2B. Thereafter, the harvesting cannula 68 is withdrawn from the body surface by retracting the harvesting tool assembly 54. The harvested follicular unit is retained in the harvesting cannula 68 as it is withdrawn from the body surface by a friction fit that may be enhanced by using a vacuum source and/or textured inner lumen wall.

As shown in FIG. 2C, as the harvesting cannula 68 exits the skin of the body surface, a distal tip of the harvesting cannula 68 is now positioned proximal of the respective grasper arm tips 73 and 75, with a harvested follicular unit (not shown) retained inside the harvesting cannula 68. A vacuum may be utilized to help draw (and thereafter retain) the harvested follicular unit into the interior lumen of the harvesting cannula 68. By actuation of the second air cylinder 62, the distal tips 73 and 75 of the arms 72 and 74 of the grasping device 52 close around the end of the harvesting cannula 68 as it exits the body surface, thereby clamping down on and, in some embodiments, cutting any tissue strands (not shown) that may remain connecting the just-harvested follicular unit and the body surface. The harvesting cannula 68 and the grasping device 52 continue to retract from the skin surface, thereby severing the connective tissue strands. Throughout this process, the fluid delivery tube 100 preferably introduces saline or another fluid into and around the distal end opening of the harvesting cannula 68, for the above-described purposes.

Figure 4:
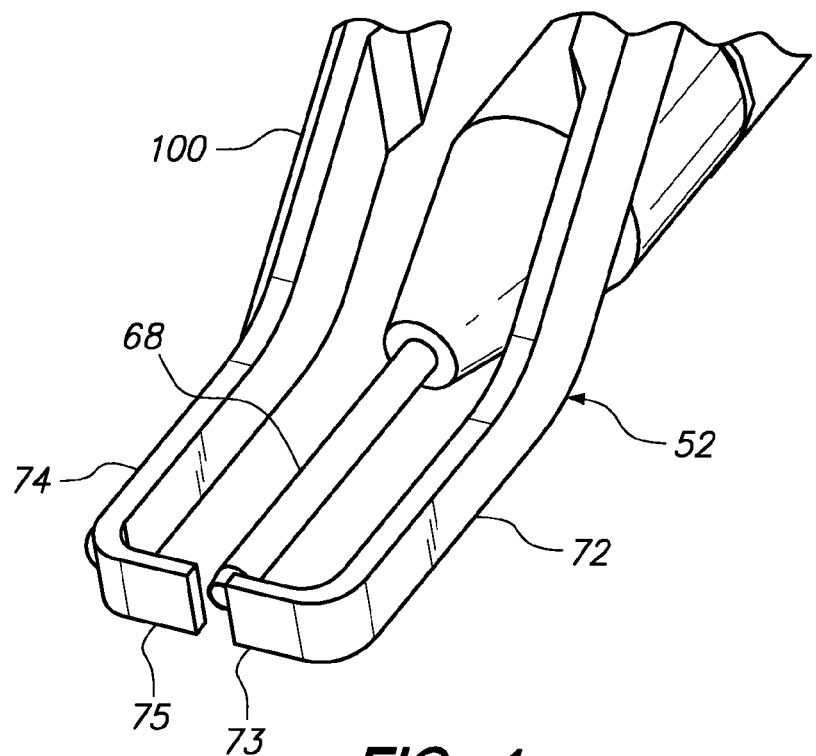
FIG. 4 is a perspective close up view of the distal portion of the harvesting tool shown in FIGS. 2A-2C, including a first embodiment of the grasping device.

As best seen in FIG. 4, it will be appreciated that the "clamping tips" 73 and 75 of arms 72 and 74 of the grasping device 52 may simply clamp between them any tissue strands which remain connecting the just-harvested follicular unit to the body surface (e.g., scalp) as they are closed, whereby continued retraction of the respective harvesting cannula and grasping device away from the body surface is what eventually breaks the tissue strands while the follicular unit is safely retained in the harvesting cannula lumen. It should also be appreciated that many variations and alterations of the grasping device 52 are possible without departing from the inventive concepts disclosed herein. By way of non-limiting examples, several alternative embodiments of the grasping device 52 having different distal arm tip configurations will now be described. It should be appreciated that the respective grasping device arm tips of the various illustrated embodiments are biased (extend) towards one another, and have respective opposing tissue engaging surfaces. It should also be appreciated that the tips may be made of many different bio-compatible materials, such as metal or hard plastic, e.g., stainless steel, polycarbonate, Teflon®, silicone, rubber.

Figure 5C:
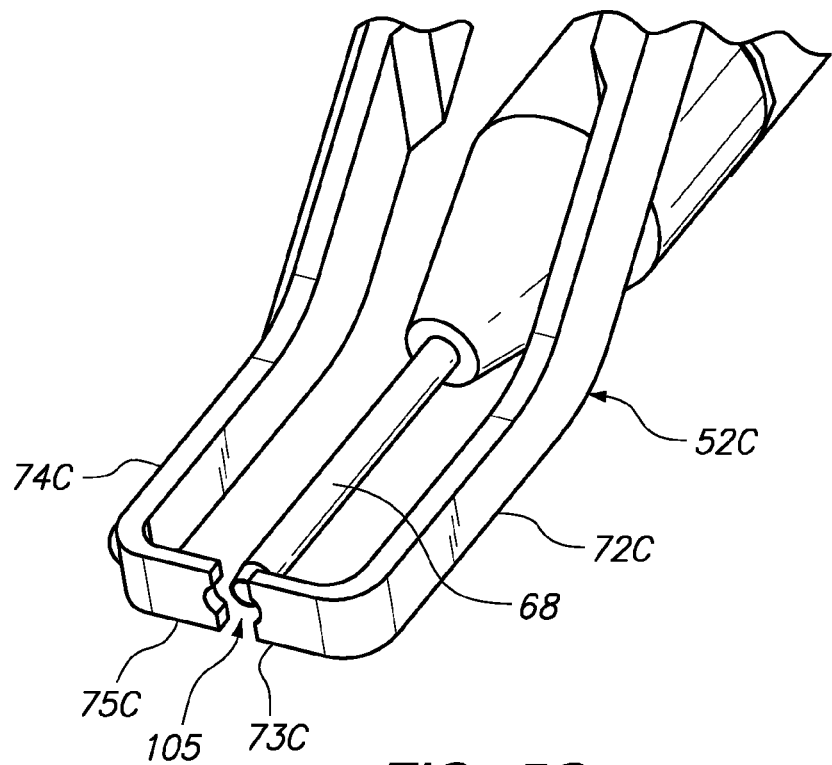

Referring to FIG. 5A, one alternative grasping device 52A has arms 72A and 74A configured with serrated grasper arm tips 73A and 75A to improve their grasping capability. FIG. 5B depicts another alternative grasping device 52B, having arms 72B and 74B with "over-center" tips 73B and 75B, respectively, which are beveled such that the beveled surfaces overlap when the grasping device 152 is in the closed position. As they close together, the beveled tips 73B and 75B may actively cut any connective tissue strand(s), e.g. in a scissor-like fashion, thereby releasing the follicular unit from the body surface without requiring additional physical pulling of the connective tissue, while minimizing potential injury to the follicular unit. FIG. 5C depicts a blunt tipped grasping device 52C wherein the tips 73C and 75C of the respective arms 72C and 74C define a center-hole 105 when the grasping device 52C is in a closed position. The center-hole 105 is sized to accommodate a wider portion of the follicular unit—and thereby prevent inadvertent cutting of—a portion of a follicular unit that may be extending from the lumen of the harvesting cannula 68.

Figure 5D:
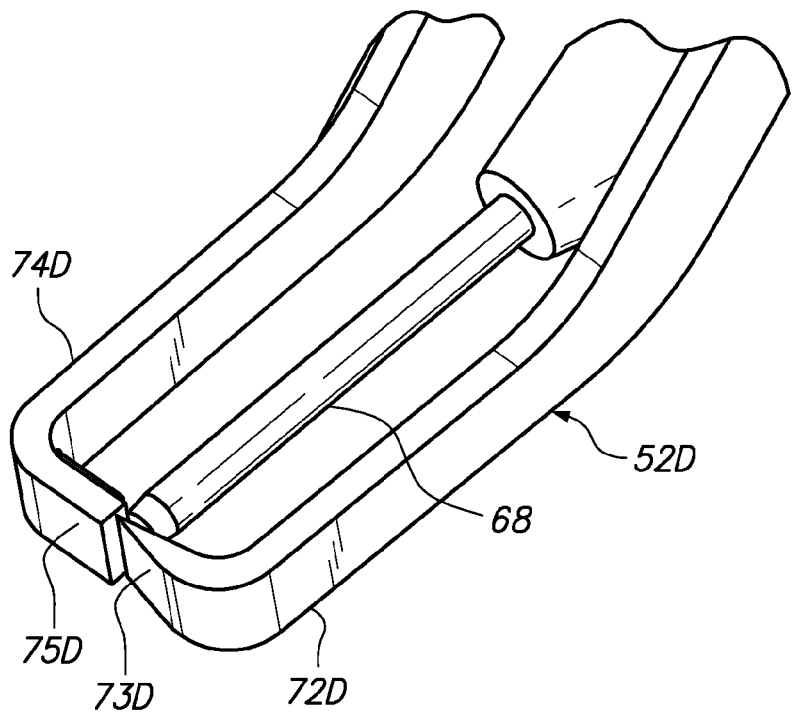
Figure 5E:
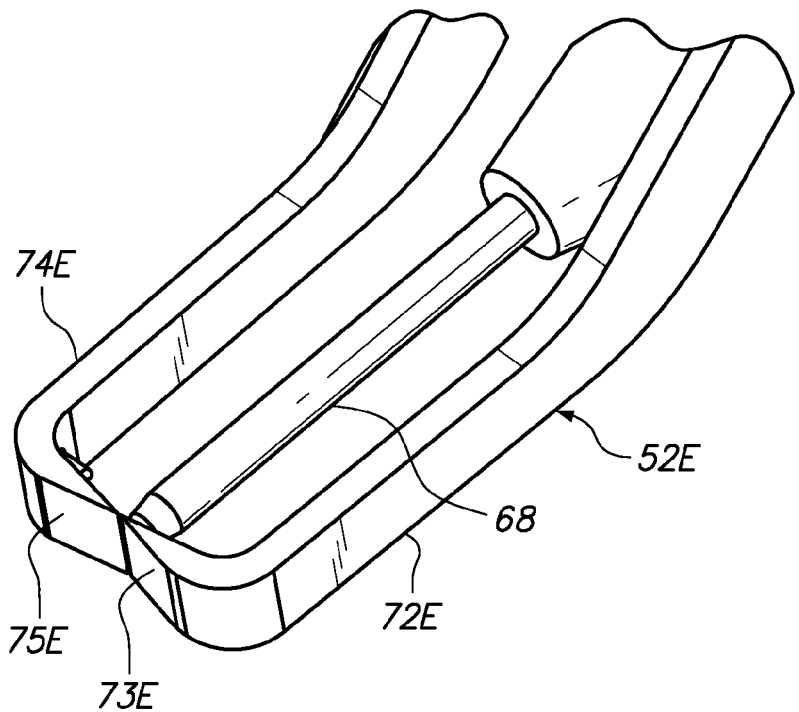

FIG. 5D depicts an embodiment of a cutting-grasping device 52D, in which one grasper arm tip 73D has a sharp cutting edge (which may be formed, for example, of sharp surgical steel), and the other tip 75D has a flat surface that functions as a blunt "chopping block" for the sharp cutting edge. The blunt surface on tip 75D may be formed of a softer material, such as Teflon® or another polymer, which facilitates the cutting action as the respective grasper arm tips 73D and 75D are closed together. FIG. 5E depicts a still further grasping device 52E, in which both grasper arms 72E and 74E have tips 73E and 75E with cutting surfaces (e.g., sharp edges) which meet and cut any connective tissue material between them as the grasping device 52E is closed.

Figure 5F:
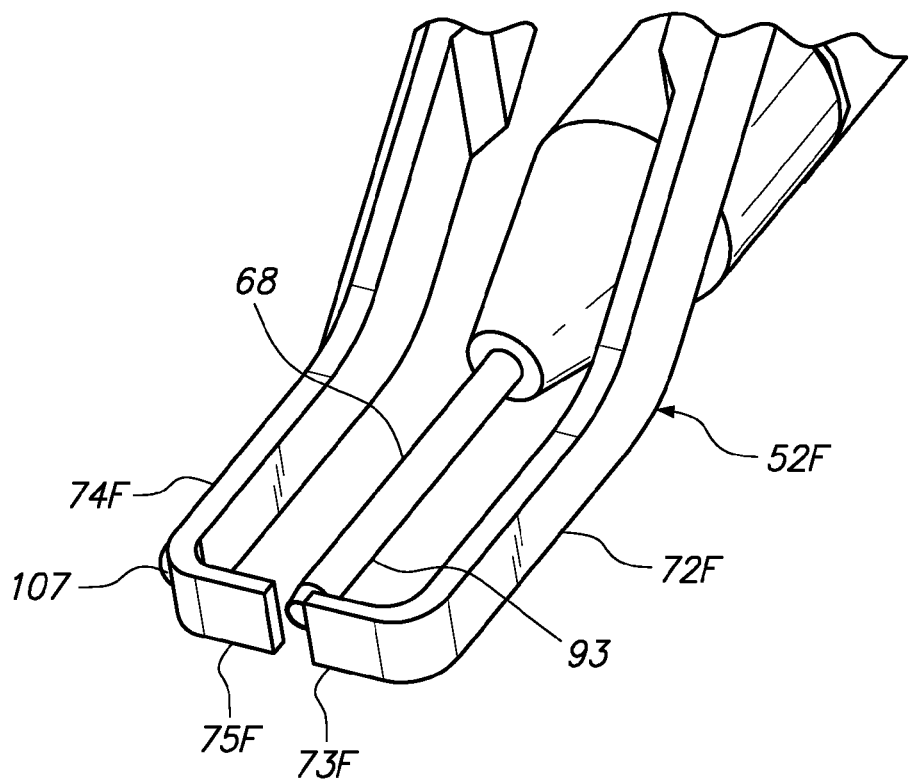
Figure 5G:
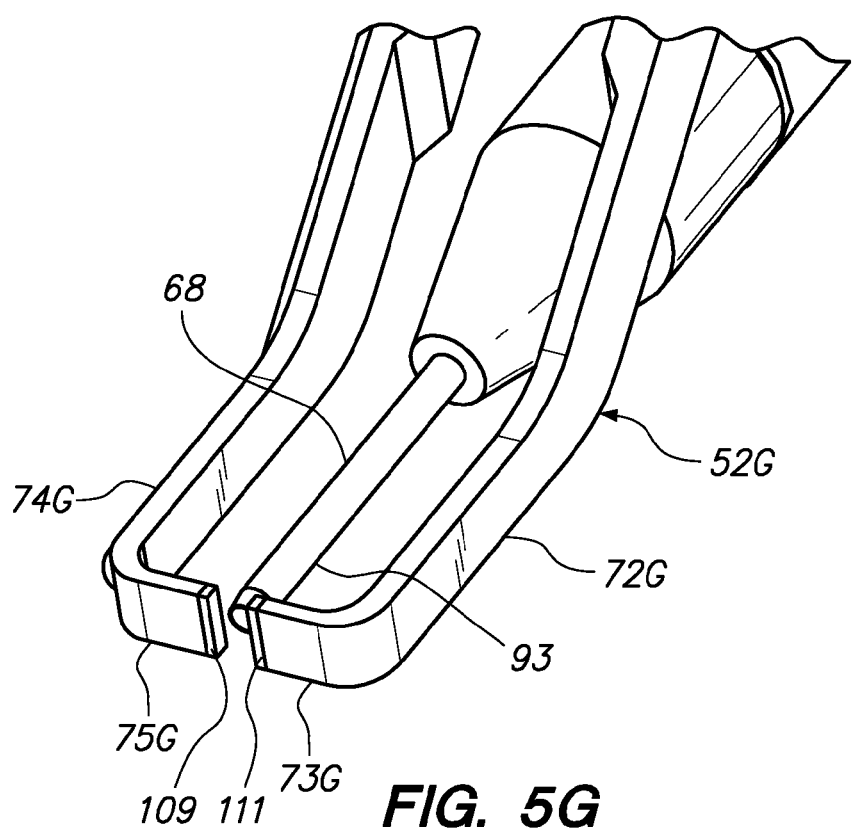
Figure 6:
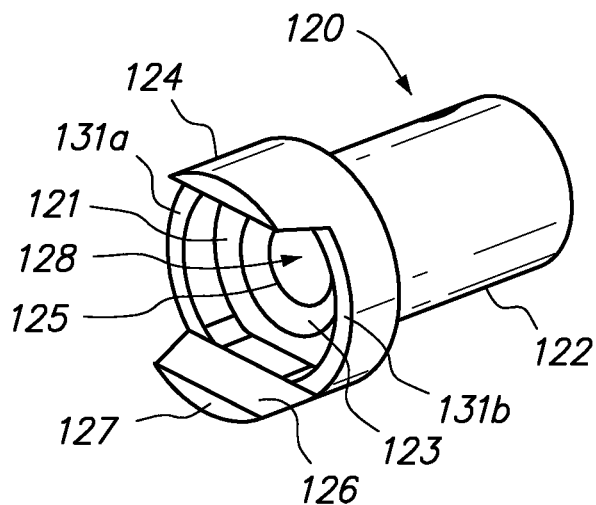
FIG. 6 is a perspective view of a follicular unit guide that may be used with (or incorporated as part of) a follicular unit harvesting tool.

FIG. 5F depicts yet another grasping device 52F, in which the tip 75F of one of the arms 74F includes an energy transmitting element 107 configured to sever a connective tissue strand when the grasping device 52F is in a closed configuration. By way of non-limiting examples, the energy transmitting element 107 may comprise an electrode for conveying radio frequency (RF) energy into the connective tissue strand (in which case a return electrode configured for attachment on the patient is also provided for completing the circuit, as is well known in the art), or alternatively the may be an ultrasound transducer for conveying acoustic wave energy into the connective tissue strand, or an optical laser source for conveying laser energy into the connective tissue strand. In each instance, the connective tissue strand is severed by energy emitted from the energy transmitting element 107. FIG. 5G depicts a still further grasping device embodiment 52G, in which one of the grasping device arm tips 75G comprises a first electrode 109, and the other tip 73G comprises a second electrode 111, the first and second electrodes 109 and 111 being configured for completing a radio frequency energy circuit through an intervening connective tissue strand engaged between the respective tips 73G and 75G when the grasping device 52G is in a closed position. It will be appreciated that the implementation and operation of the respective energy transmitting elements and electrodes (107, 109, 111) in the devices 52F and 52G of FIGS. 5F and 5G may be carried out according to well-known techniques and apparatus, and need not be elaborated upon herein. By way of one, non-limited example, the energy dosing level may be in a range of approximately 3-10 watts applied (for example) for up to 1 second. Notably, the tissue-severing energy should be applied at a location sufficiently below the bulb of the harvested follicular unit so that the follicular unit itself is not harmed or damaged during the connective tissue severing process.

Referring generally to FIGS. 6 and 7A-D, in some embodiments, a follicular unit harvesting tool 170 further comprises a guide member 120 that works in conjunction with the grasping device 152 to help capture and retain harvested follicular units (not shown in the Figures). In one embodiment (best seen in FIG. 6), the guide member 120 has an elongate cylindrical body 122 defining an axial passageway 128 through which the harvesting cannula 168 extends. The guide member body 122 may further define an interior bore 121 within its distal end, the bore 121 having a proximal tapered portion 123 leading to an opening 125 in communication with the axial passageway 128. A distal facing end 127 of the guide member body 122 includes spaced apart extensions 124 and 126 that have flat inward facing surfaces configured to mate with the grasping device arm tips 173 and 175 (best seen in FIG. 7C), with respective arcuate end surfaces 131a and 131b spanning between extensions 124 and 126 form a "stop" to limit distal motion of the guide member 120 relative to the (closed) grasping device arm tips 173 and 175.

Figure 7A:
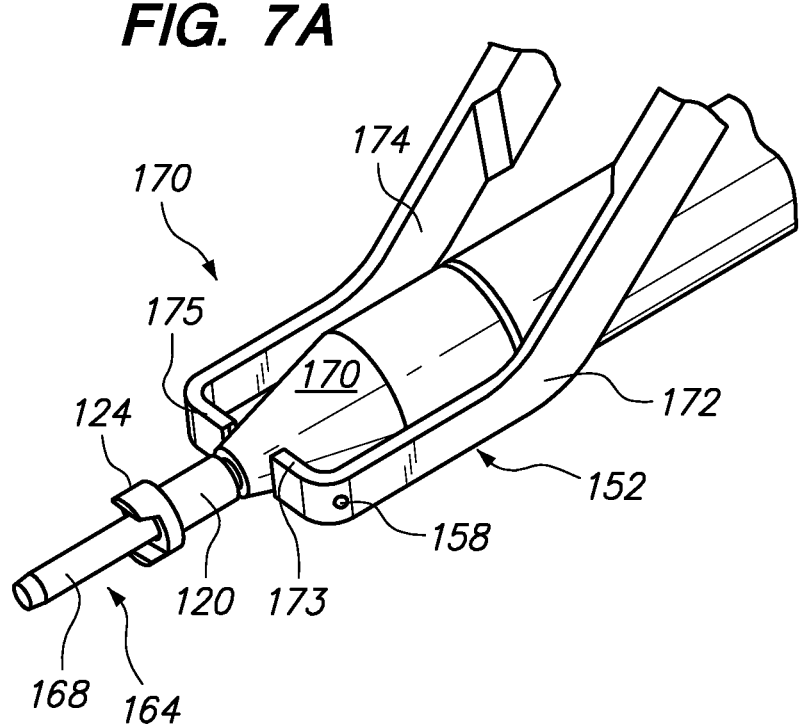
FIGS. 7A-7D are perspective views of an exemplary embodiment of a follicular unit harvesting tool incorporating a grasping device along with the follicular unit guide shown in FIG. 6.

Referring specifically to FIG. 7A, the guide member 120 is shown incorporated into the follicular unit harvesting device 170. The harvesting tool further comprises a respective grasping device 152 and harvesting tool assembly 154, which are configured and may be controlled in the same manner as the respective grasping device 52 and harvesting tool assembly 54 of the above-described harvesting tool 50. Briefly, the harvesting tool assembly 154 comprises a harvesting cannula 168 extending from a hub 170, wherein the harvesting cannula 168 is movable relative to the grasping device 152 and guide member 120, and extends through the axial passage 128 and distal interior bore 121 of the guide member 120. The grasping device 152 has a pair of arms 172 and 174 which extend proximally from respective distal tips 173 and 175 to an actuating system (not shown) that controls movement of the grasping device from an open position, in which the arm tips 173 and 175 are separated (shown in FIG. 7A), and a closed position, in which the arm tips 173 and 175 are positioned in close proximity to each other and beyond the distal end of the harvesting cannula 168 (shown in FIGS. 7B and 7C). The harvesting tool 170 is shown in a "harvest ready" configuration in FIG. 7A, with the distal end of the harvesting cannula 168 extending through the open distal end 127 of the guide member 120 and beyond the open grasper arms 172 and 174 for harvesting a follicular unit from a body surface (not shown). A fluid (e.g., saline) delivery port 158 is also depicted on a distal end of one of the grasper arms 172. However, it should be appreciated that the illustrated location of the fluid delivery port 158 is merely one example, and that one or more fluid delivery ports may be provided at other locations on the grasping device 152, as is the case with other embodiments depicted herein.

Figure 7B:
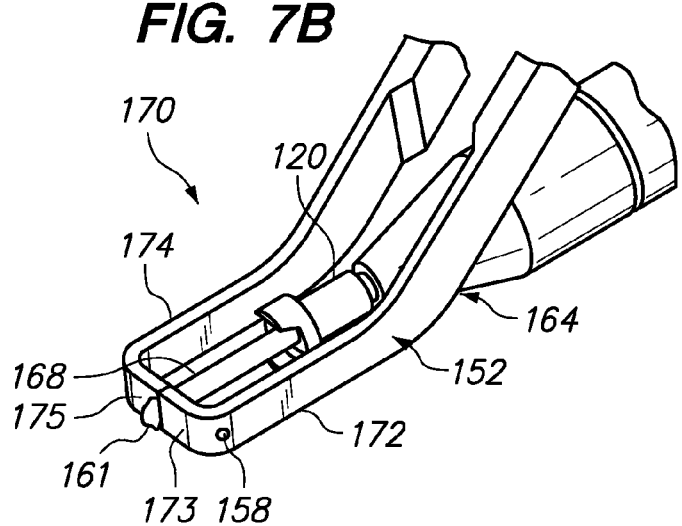

Referring to FIG. 7B, following the harvesting of a follicular unit, the harvesting cannula 168 is retracted relative to the grasping device 152, which is moved to its closed position. For purposes of illustration only, a piece of tissue 161 is shown extending from between the closed grasper arm tips 173 and 175, which tissue 161 may be a portion of the harvested follicular unit, a connective tissue strand attached to the harvested follicular unit, or both. It will be appreciated that the closing force on the tips 173 and 175 is minimized to prevent damaging the tissue 161 in the event it is (at least in part) a portion of the harvested follicular unit.

Figure 7C:
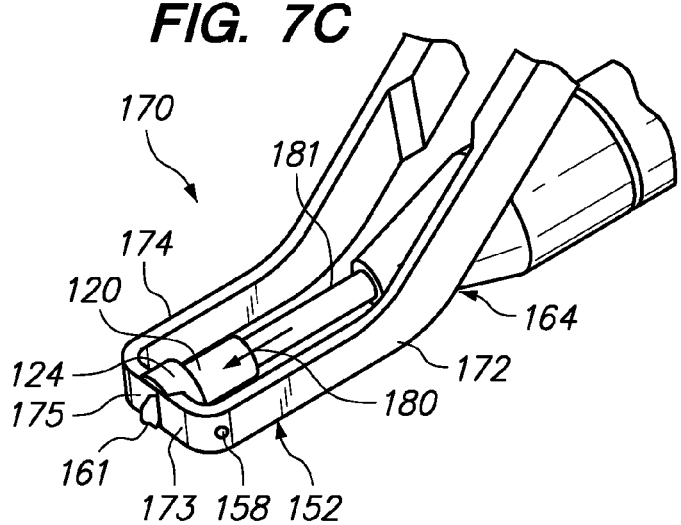

Referring to FIG. 7C, while the grasping device 152 remains in the closed position, the guide member 120 is moved distally along the harvesting cannula 168 (as indicated by arrow 180), until the distal facing end 127 of the guide member 120 mates with the closed grasping device arm tips 173 and 175, resulting in the distal end of the harvesting cannula 168 being positioned within the interior bore 121 of the guide member 120. In particular, the mated guide member 120 and grasper arm tips 173 and 175 at least partially seal the interior bore 121 of the guide member 120, thereby enhancing a pulling force of a vacuum source in communication with the harvesting cannula lumen. The grasping device 152 then begins to return to the open position, releasing the follicular unit as the arm tips 173 and 175 separate, and the harvested follicular unit is drawn into a more proximal interior region of the harvesting cannula assembly 154 due to the built-up enhanced vacuum pulling force. It should be appreciated that relative movement of the guide 120 over the harvesting cannula 168 may be accomplished by an automated mechanism or by manual manipulation. For example, a small air cylinder could actuate the guide member, 120, along the harvesting cannula, 168.

Figure 7D:
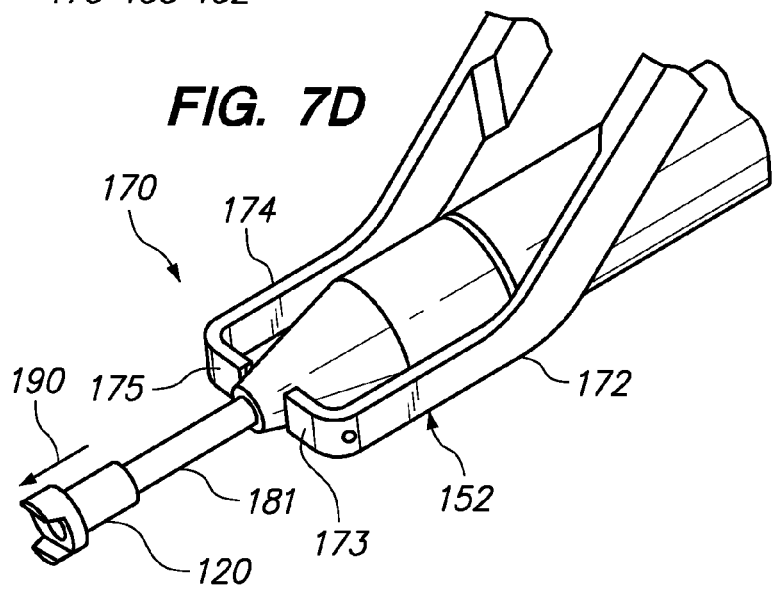

Referring to FIG. 7D, generally after the opening of the grasping device arms 172 and 174, the guide member 120 is further advanced distally over the harvesting cannula 168 (indicated by arrow 190), although it will be appreciated that the harvesting cannula 168 can be retracted relative to the guide member 120 to accomplish the same relative motion. In particular, the axial passageway 128 of the guide member 120 has an inner diameter sufficiently close to an outer diameter of the harvesting cannula 168 such that any remaining tissue associated with the harvested follicular unit extending outwardly from the cannula distal end is dislodged inwardly at the opening 125 as the cannula distal end is withdrawn from the interior bore 121 and into the axial passageway 128. Similarly, any tissue associated with the harvested follicular unit that may be stuck or adhered to the grasper arm tips 173 and 175 is dislodged as the respective tips open and move laterally over the distal arcuate edges 131a and 131b of the guide member 120. It should be appreciated that the guide member 120 can have the further advantage of directing a greater quantity of fluid (e.g., saline) into the harvesting cannula lumen due to its "funnel-like" configuration.

Figure 8A:
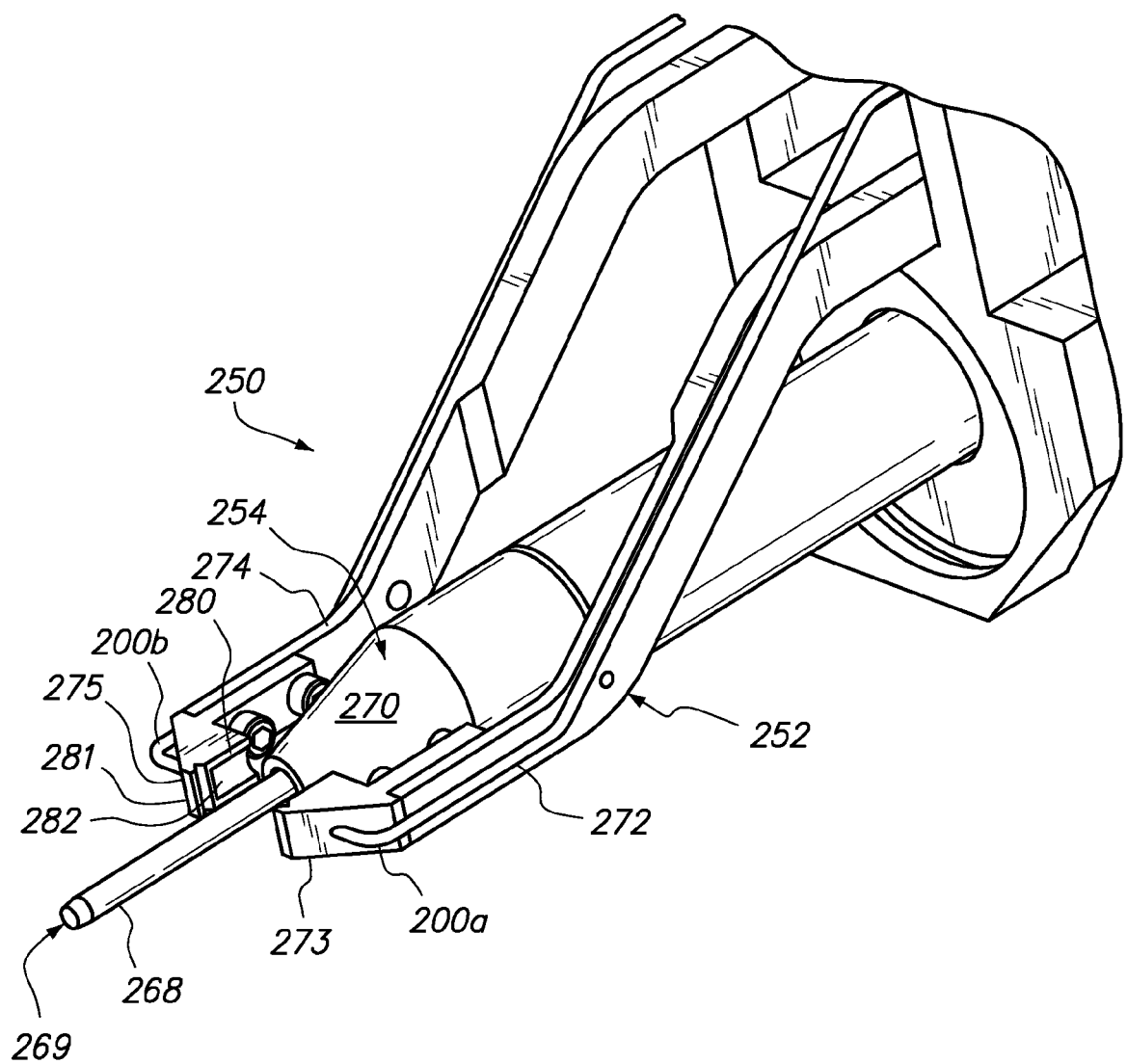
FIGS. 8A-8C are perspective views of still another exemplary embodiment of a follicular unit harvesting tool, including a grasping device.
Figure 8B:
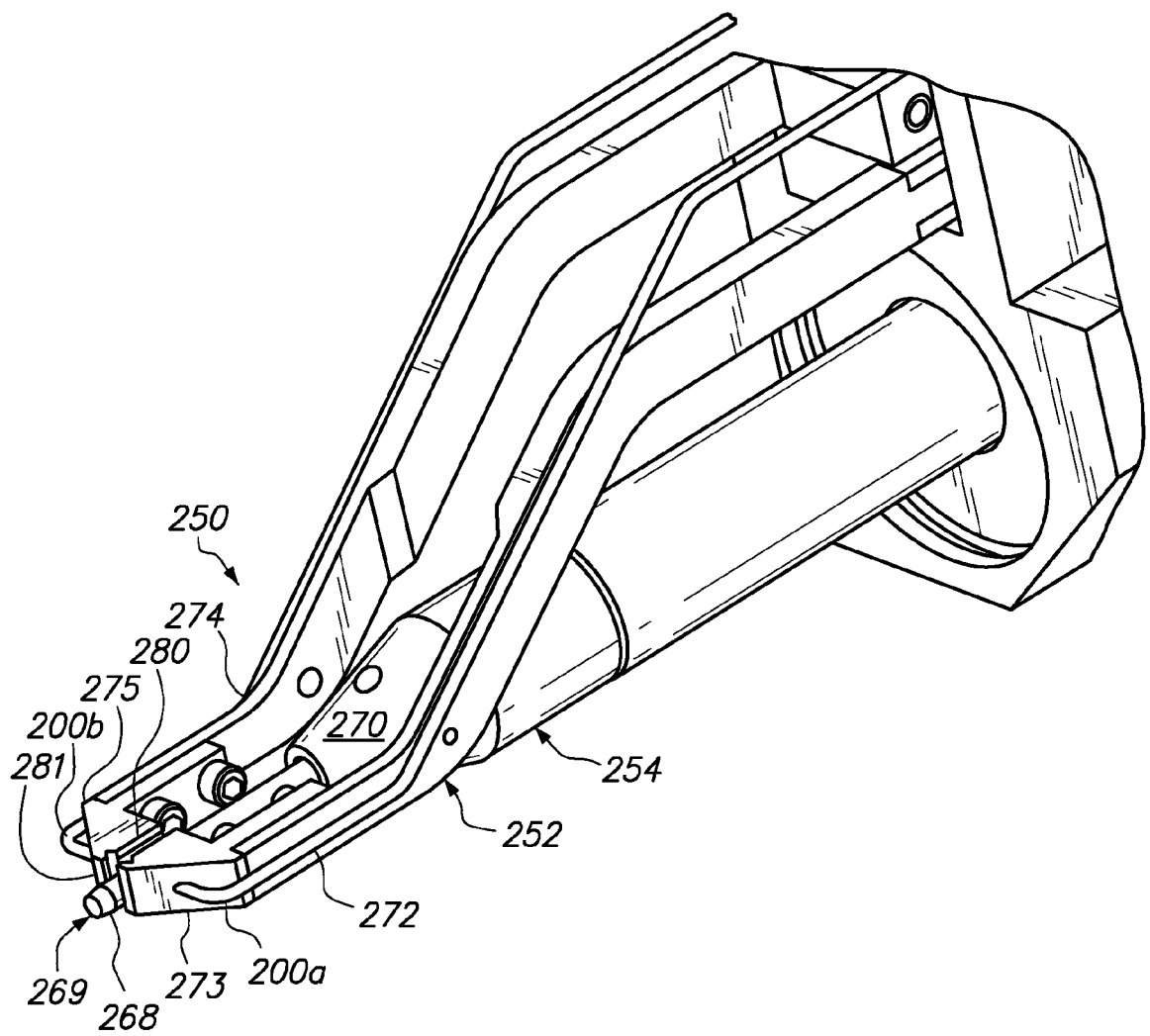
Figure 8C:
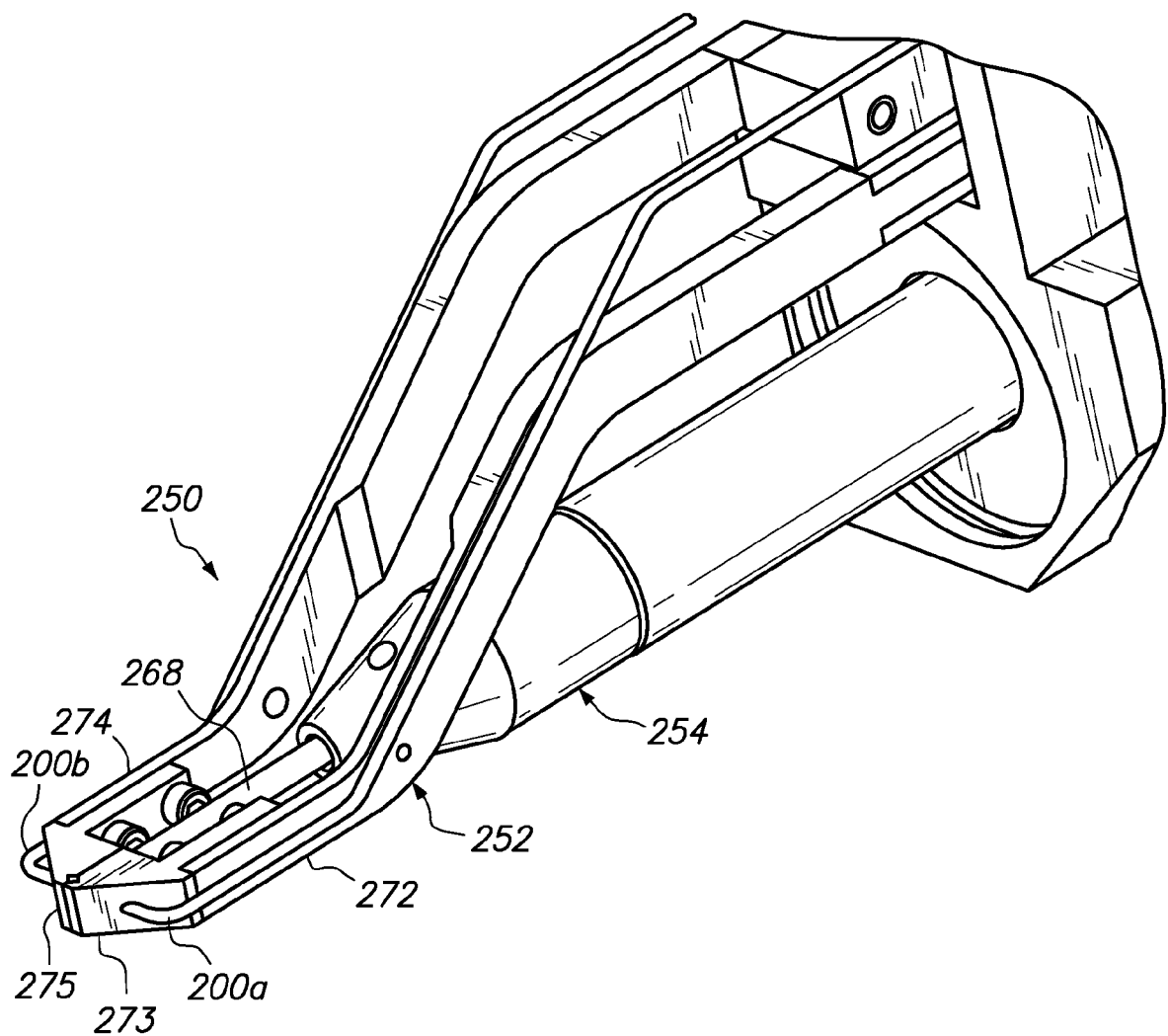

FIGS. 8A-8C are perspective views of still another exemplary embodiment of a follicular unit harvesting tool 250, including a grasping device 252 and a harvesting tool assembly 254. The grasping device 252 and harvesting tool assembly 254 are similarly configured to, and may be controlled in the same manner as, the respective grasping device 52 and harvesting tool assembly 54 of the above-described harvesting tool 50. The harvesting tool assembly 254 comprises a harvesting cannula 268 extending from a hub 270, wherein the harvesting cannula 268 is movable relative to the grasping device 252. The grasping device 252 has two arms 272 and 274 extending proximally from respective distal tips 273 and 275 to an actuating system (not shown) that controls movement of the grasping device 252 from an open position, in which the arm tips 273 and 275 are separated (shown in FIG. 8A), and a closed position, in which the arm tips 273 and 275 are positioned in close proximity to each other and beyond the distal end of the harvesting cannula 268 (shown in FIGS. 8B and 8C).

In accordance with this embodiment, the respective grasping device arm tips 273 and 275 comprise opposing tissue engaging surfaces 280 having corresponding grooves 282 formed in a proximal portion thereof. While the respective tissue engaging surface 280 and groove 282 formed therein are only visible in tip 275 because of the angle of the perspective view in FIGS. 8A-8C, it should be appreciated that the unseen tissue engaging surface 280 and groove 282 on tip 273 are essentially a mirror image of the same components on tip 275. The respective grooves 282 on the surfaces 280 of tips 273 and 275 define a cavity for receiving a distal end portion of the harvesting cannula 268 when the grasping device 252 is in the closed position, and the respective tissue engaging surfaces 280 are brought together (shown in FIG. 8C). The respective grooves 282 are preferably dimensioned so that the resulting cavity snuggly seats the distal end of the harvesting cannula 268 to at least partially seal its open distal end 269 and thereby enhance a pulling force of a vacuum source in communication with the inner harvesting cannula lumen. The tissue engaging surfaces 280 of the grasper arm tips 273 and 275 each may further comprise a distal serrated portion 281 to improve their grasping capability when the grasping device 252 is in the closed position (shown in FIG. 8C).

The follicular unit harvesting tool 250 may further include a first fluid conduit 200a coupled to grasping device arm 272, and a second fluid conduit 200b coupled to grasping device arm 274. The first and second fluid conduits 200a and 200b have respective outlets (not shown in the Figures) located in an inner wall of the respective tissue engaging surface grooves 282 of the respective tissue engaging surfaces 280 for delivering fluid into the cavity formed by grooves 282 when the grasping device 252 is in the closed position. Directing fluid into the cavity while the grasping device 252 is in a closed position will help seal the open distal end of the cannula 269 and improve the pulling force of a vacuum source in communication with the interior harvesting cannula lumen. It will be appreciated that alternate embodiments may employ only a single, or multiple (or no) fluid conduit, have different configurations and shapes of such one or more fluid conduits, as well as use different methods and ways of attaching such fluid conduits, moreover the fluid outlet ports may be placed in other locations.

In accordance with a particular aspect of this embodiment, the outward facing sides of the respective grasping device arm tips 273 and 275 are tapered to their respective distal ends so as to form an arrow-shape when the grasping device 252 is in the closed position. As seen in FIG. 8B, the grasping device arms 272 and 274 are moveable along the outer surface of the harvesting cannula 268 when in their open position so that the respective distal ends of the grasper arm tips 273 and 275 may be inserted into a body surface to a depth beyond an insertion depth of the distal end 269 of the harvesting cannula 268 when harvesting a follicular unit. In this manner, as seen in FIG. 8C, the respective tissue engaging surfaces 280 of the grasping device arm tips 273 and 275 can then be moved into the closed position to retain the harvested follicular unit within the interior lumen of the harvesting cannula 268, and within the cavity formed by the grooves 282 in the respective tissue engaging surfaces 280 of the grasper arm tips 272 and 274, as the respective harvesting cannula 268 and grasping device 252 are moved out of the body surface.

Figure 10:
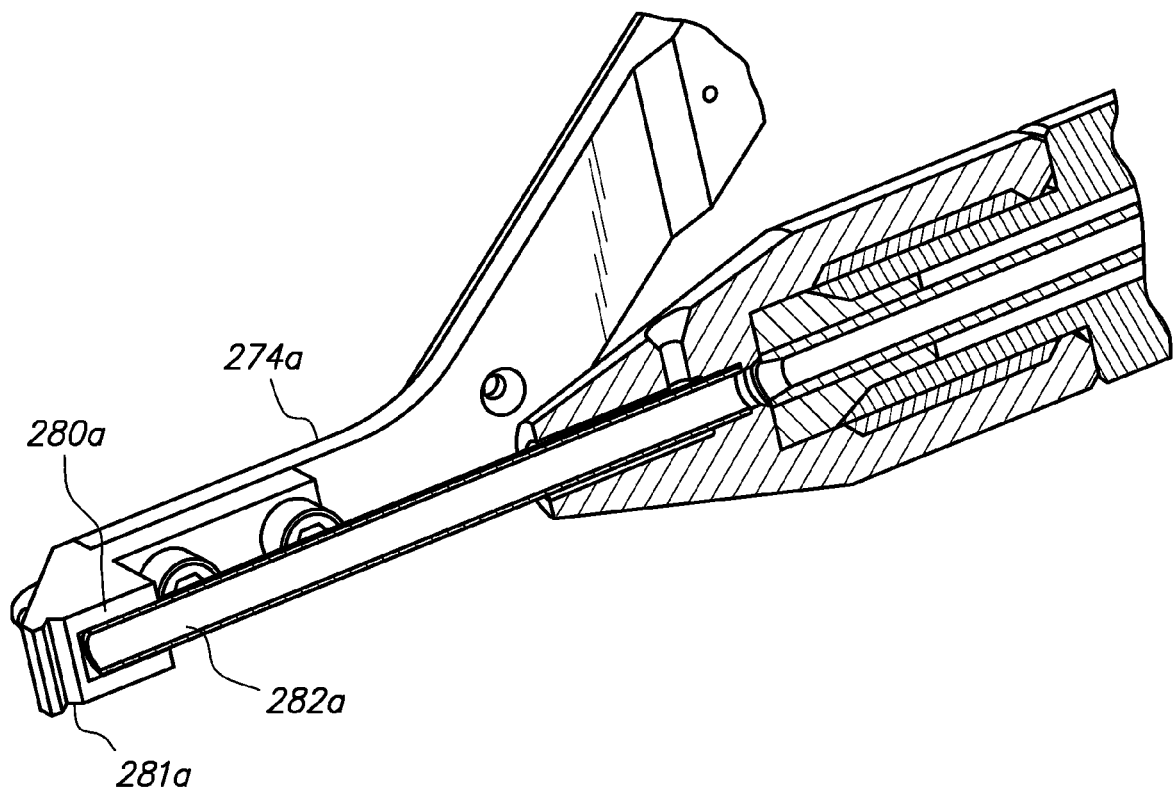
FIG. 10 is a perspective view of an inner side of an arm of an alternate tissue grasping device for use in the follicular unit harvesting tool of the present invention.

In an alternate embodiment shown in FIG. 10, to facilitate sliding of the grasping device arms along the harvesting cannula, the "groove" in the tissue grasping surface (designated as 280a in FIG. 10) may extend as a smooth channel 282a from the distal grasping portion 281a of the surface 280a proximally along the entire length (or, in some alternative embodiments, any portion thereof) of the grasper arm (designated as 274a in FIG. 10).

Figure 9:
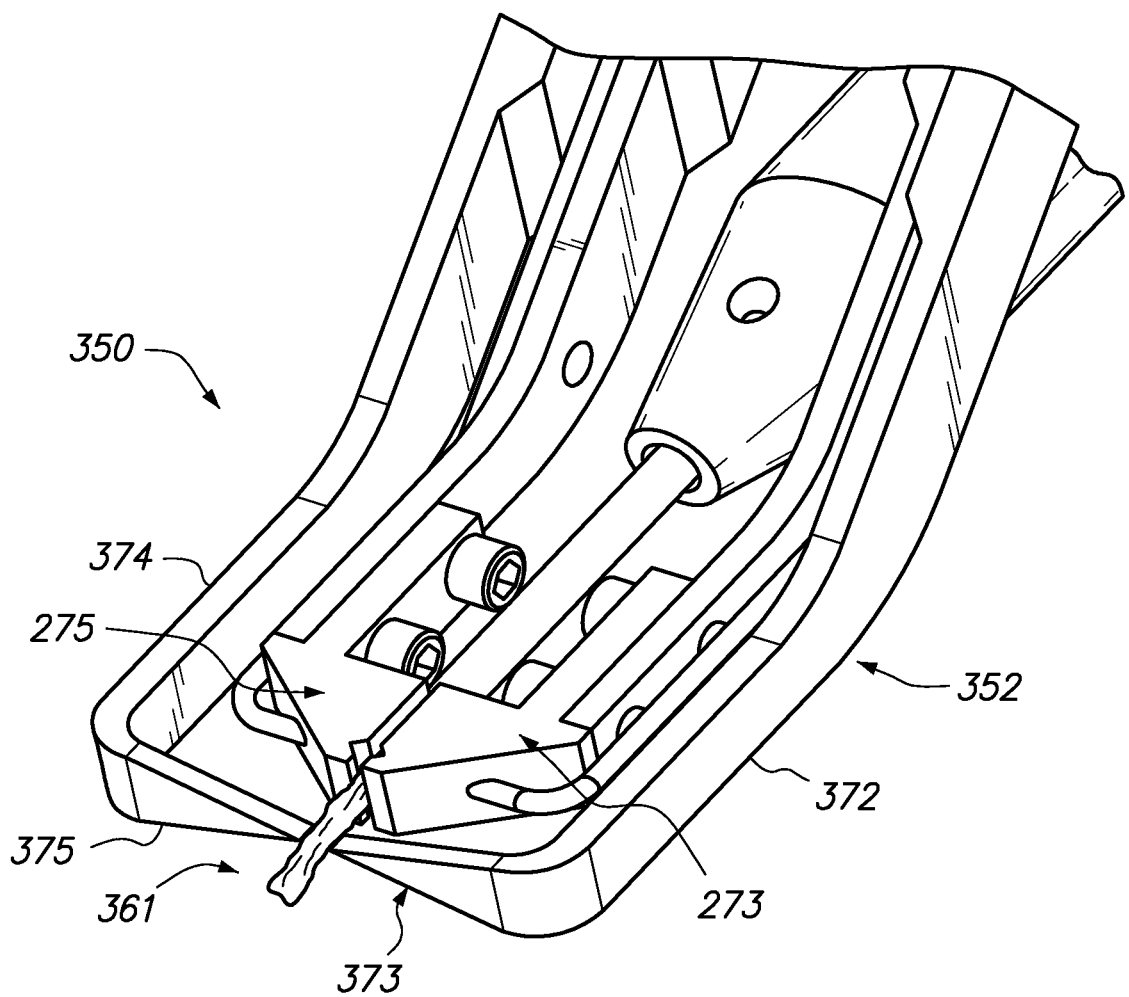
FIG. 9 is a perspective view of a modified embodiment of the follicular unit harvesting tool shown in FIGS. 8A-8C, including an additional grasper device that employs an energy transmitting element to sever any connective tissue strands while the first grasper retains the harvested follicular unit.

FIG. 9 is a perspective view of a modified embodiment of the follicular unit harvesting tool 250 shown in FIGS. 8A-8C (and given reference number 350 in FIG. 9). In particular, the tool 350 includes an additional grasper device 352 that has respective arms 372 and 374 surrounding the grasper device 252. The arms 372 and 374 extend to inwardly directed distal tips 373 and 375, respectively, wherein one or both of the tips 373 and 375 employs an energy transmitting element to sever any connective tissue strands 361 while the first grasper arm tips 273 and 275 retain the harvested follicular unit. As with the above-described embodiments of FIGS. 5F and 5G, the energy transmitting element carried by one or both of the tips 373 and 375 may be, by way of non-limiting example, an electrode for transmitting RF energy, an ultrasound transducer for transmitting mechanical wave energy, or a laser for transmitting optical energy. In one variation of the embodiment shown in FIG. 9, a first one of the second grasping device arm tips 273 comprises a first electrode, and the other tip 275 comprises a second electrode, the first and second electrodes configured for completing a radio frequency energy circuit through the connective tissue strand 361 to thereby sever same.

It should be appreciated from the foregoing description taken in conjunction with the accompanying figures that various methods for harvesting follicular units from a body surface using a follicular unit harvesting tool incorporating a grasping device have also been disclosed. To further summarize such disclosed methods, by way of non-limiting example, a method according to one embodiment of the invention includes the acts of: (i) inserting a distal end of a harvesting tool into the body surface to surround and core a follicular unit (ii); withdrawing the distal end of the harvesting tool from the body surface with the follicular unit at least partially retained in an interior lumen of the harvesting tool; and (iii) moving one or both of a grasping device operatively associated with the harvesting tool and the harvesting tool relative to each other so that two arm tips of a pair of opposing arms of the grasping device extend beyond the distal end of the harvesting tool and in close proximity to each other to facilitate grasping and/or severing of a connective tissue strand connecting the follicular unit to the body surface.

In one such embodiment, the method includes applying energy to the connective tissue strand through an energy transmitting element operatively connected to at least one arm of the grasping device to sever the connective tissue strand from the follicular unit. By way of non-limiting example, one of the grasping device arms may have a tissue engaging tip comprising a first electrode, and the other tissue engaging tip comprising a second electrode, wherein the connective tissue strand is severed by completing a radio frequency energy circuit through the strand via the respective electrodes.

In another such embodiment the grasping device comprises a first tissue grasping device, and the method includes engaging the follicular unit and the connective tissue strand with the first tissue grasping device, and delivering energy to sever the connective tissue strand via an energy transmitting element operatively connected to at least one arm of a second tissues grasping device.

In a further embodiment, the arms of the grasping device have corresponding grooves to define a cavity, and the method includes moving the harvesting tool and/or the grasping device relative to each other such that the distal end of the harvesting tool is received within the cavity. Preferably, the cavity is dimensioned to at least partially seal the enclosed open distal end portion of the harvesting tool within the cavity to thereby enhance a pulling force of a vacuum source in communication with the harvesting tool lumen.

In one additional embodiment, the method includes moving the grasping device relative to the harvesting tool, for example, a harvesting cannula to thereby insert the respective arm tips of the grasping device into the body surface to a depth beyond an insertion depth of the distal end of the harvesting tool, and closing tissue engaging surfaces of the grasping device arm tips to retain the harvested follicular unit within the harvesting tool as the harvesting tool is retracted from the body surface.

In another embodiment, a method for harvesting follicular units from a body surface includes (i) positioning an open, tissue-coring distal end of a harvesting cannula proximate a follicular unit to be harvested; (ii) inserting the harvesting cannula distal end into the body surface, surrounding and thereby coring the follicular unit; (iii) withdrawing the harvesting cannula distal end from the body surface with the follicular unit at least partially retained in an interior lumen of the harvesting cannula; (iv) closing opposing tissue engaging surfaces of a grasping device operatively associated with the harvesting cannula to thereby engage a portion of the follicular unit extending out of the open distal end of the cannula and/or a connective tissue strand connecting the follicular unit to the body surface; and severing the connective tissue strand by retracting the grasping device from the body surface.

Various follicular harvesting methods according to the disclosed invention may include delivering fluid (such as saline) through a fluid conduit coupled to the grasping device, the fluid conduit having an outlet positioned for delivering fluid proximate the distal end of the harvesting tool. The fluid may provide several benefits, including flushing away excess tissue and blood around the area of the harvested follicular unit on the body surface, providing moisture to the follicular unit, lubricating a pathway of the follicular unit within the harvesting cannula, and helping to seal the distal end of the harvesting cannula surrounding a harvested follicular unit to increase the pulling force of a vacuum source in communication with the interior harvesting cannula lumen.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular feature or characteristic described in reference to one figure or embodiment may be combined as suitable with features or characteristics described in another figure or embodiment. Similarly, the invention is not limited to the use of a robotic system including a robotic arm, and that other automated and semi-automated systems may be utilized.

By way of non-limiting example, it will be appreciated by those skilled in the art that the invention is not limited to the use of a robotic system, and that other automated, semi-automated, and manual systems and apparatus may be used for positioning and actuating the respective harvesting cannulas and other devices and components disclosed herein. By way of another example, it will be appreciated by those skilled in the art that while the foregoing harvesting tool embodiments are described herein in the context of harvesting hair follicular units, the tools are not limited to the harvesting of hair follicular units, and may be equally used for removing dermal and sub-dermal tissue plugs that do not contain hair follicular units.

What is claimed is:

1. A follicular unit harvesting tool, comprising:
a tool housing;
a hair harvesting cannula extending from the tool housing, the hair harvesting cannula having an interior lumen sized for harvesting individual follicular units and an open distal end in communication with the lumen, the distal end having a coring edge configured to dissect tissue to encapsulate a follicular unit in the lumen of the harvesting cannula; and
a grasping device extending from the tool housing and having at least two arms, each arm extending to a respective tip, one or both of the harvesting cannula and grasping device being movable with respect to the tool housing and relative to the other, the grasping device having an open position in which the arm tips are separated and a closed position in which the arm tips are positioned in close proximity to each other and beyond the distal end of the hair harvesting cannula, the grasping device being configured to grasp and/or sever a connective tissue strand connecting a follicular unit to a body surface from which the follicular unit was harvested; and
an actuation system accommodated by the tool housing and configured to provide controlled lateral and longitudinal movement of the arms of the grasping device such that each arm is allowed to move laterally without simultaneously moving the grasping device or a portion thereof longitudinally.

2. The follicular unit harvesting tool of claim 1, the grasping device arm tips comprising respective opposing tissue engaging surfaces.

3. The follicular unit harvesting tool of claim 2, wherein the respective tissue engaging surfaces are serrated surfaces that mate when the grasping device is in the closed position.

4. The follicular unit harvesting tool of claim 2, wherein the respective tissue engaging surfaces define a center-hole when the grasping device is in the closed position, the center-hole being sized to accommodate a portion of a follicular unit extending from the lumen of the harvesting cannula.

5. The follicular unit harvesting tool of claim 2, the respective tissue engaging surfaces of the grasping device arm tips having corresponding grooves formed therein, the grooves defining a cavity for receiving a distal end portion of the harvesting cannula when the grasping device is in the closed position.

6. The follicular unit harvesting tool of claim 5, wherein the fluid conduit outlet is located in an inner wall of the respective tissue engaging surface groove of the grasping arm tip for delivering fluid into the cavity when the grasping device is in the closed position.

7. The follicular unit harvesting tool of claim 5, further comprising a vacuum source in communication with the harvesting cannula lumen and wherein the cavity is dimensioned to at least partially seal the distal end portion of the harvesting cannula enclosed within the cavity when the grasping device is in the closed position and to enhance a pulling force of the vacuum source.

8. The follicular unit harvesting tool of claim 2, wherein outer sides of the respective grasping device arm tips are tapered to their respective distal ends so as to form an arrow-shape when the grasping device is in the closed position, and wherein the grasping device arms are moveable relative to the harvesting cannula to insert the respective distal ends of the grasper arm tips into the body surface to a depth beyond an insertion depth of the distal end of the harvesting cannula when harvesting a follicular unit, and the respective tissue engaging surfaces of the grasping device arm tips are movable into the closed position to retain the harvested follicular unit within the harvesting cannula as the respective harvesting cannula and grasping device are retracted from the body surface.

9. The follicular unit harvesting tool of claim 1, wherein one or both grasping device arm tips comprise a tissue cutting surface.

10. The follicular unit harvesting tool of claim 9, wherein the respective grasping device arm tips are beveled and configured to overlap and cut the connective tissue strand as the grasping device is moved from the open position to the closed position.

11. The follicular unit harvesting tool of claim 9, wherein the grasping device arm tips comprise respective tissue cutting surfaces configured to overlap and cut the connective tissue strand in a scissor-like action as the grasping device is moved from the open position to the closed position.

12. The follicular unit harvesting tool of claim 1, wherein one of the grasping device arm tips comprises a tissue cutting surface, and the other comprises a dull surface configured to meet the tissue cutting surface when the grasping device is in the closed position to facilitate cutting of the tissue strand.

13. The follicular unit harvesting tool of claim 1, at least one of the grasping device arm tips comprising an energy transmitting element configured to sever the connective tissue strand.

14. The follicular unit harvesting tool of claim 13, the energy transmitting element selected from the group comprising an electrode, an ultrasound transducer, and a laser.

15. The follicular unit harvesting tool of claim 13, wherein one of the grasping device arm tips comprises a first electrode, and the other comprises a second electrode, the first and second electrodes configured for completing a radio frequency energy circuit through the connective tissue strand to thereby sever same.

16. The follicular unit harvesting tool of claim 1, the tissue grasping device comprising a first tissue grasping device, and further comprising a second tissue grasping device having a pair of opposing arms extending to respective tissue engaging tips, at least one of the second tissue grasping device arm tips comprising an energy transmitting element configured to sever the connective tissue strand while the first tissue grasping device is in the closed position.

17. The follicular unit harvesting tool of claim 16, wherein one of the second grasping device arm tips comprises a first electrode, and the other comprises a second electrode, the first and second electrodes configured for completing a radio frequency energy circuit through the connective tissue strand to thereby sever same.

18. The follicular unit harvesting tool of claim 1, wherein the harvesting cannula comprises two axially aligned cannulas.

19. The follicular unit harvesting tool of claim 1, further comprising one or more of a mechanical system, electromechanical system, pneumatic system, hydraulic system or a magnetic system for effecting movement of the harvesting cannula and/or grasping device relative to one another.

20. The follicular unit harvesting tool of claim 1, further including a system in the tool housing for effecting rotational movement of the harvesting cannula about its longitudinal axis.

21. The follicular unit harvesting tool of claim 1, wherein the harvesting tool is part of a robotic system, the robotic system comprising a robotic arm capable of movement in a plurality of directions and a processor configured to maneuver the robotic arm to automatically position the harvesting tool.

22. The follicular unit harvesting tool of claim 1, wherein the actuation system further effects movement of the harvesting cannula and grasping device with respect to the tool housing and relative to one another.

23. A follicular unit harvesting tool, comprising:
a tool housing;
a hair harvesting cannula extending from the tool housing, the hair harvesting cannula having an interior lumen sized for harvesting individual follicular units and an open distal end in communication with the lumen, the hair harvesting cannula being axially stiff with the distal end having a coring edge configured to dissect tissue to encapsulate a follicular unit in the lumen of the hair harvesting cannula; and
a grasping device having two arms, each arm extending from the tool housing separate from and alongside the cannula to a tip, the tips of the arms presenting a blunt distal surface, both the harvesting cannula and grasping device being movable with respect to the tool housing and relative to the other, the grasping device having an open position in which the arm tips are separated and a closed position in which the arm tips are positioned in close proximity to each other and beyond the distal end of the harvesting cannula, the blunt distal surface having a configuration that prevents the tips of the arms from penetrating skin in both the open and closed positions, the grasping device being configured to grasp a connective tissue strand connecting a follicular unit to a body surface from which the follicular unit was harvested by the cannula and after the cannula has been retracted from the skin.

24. The follicular unit harvesting tool of claim 23, further comprising a guide member having an axial passageway through which the harvesting cannula extends, a distal interior bore in communication with the axial passageway, and a distal facing end configured to mate with the grasping device arm tips when the grasping device is in the closed position so as to at least partially seal the interior bore and thereby enhance a pulling force of a vacuum source in communication with the harvesting cannula lumen when the distal end of the harvesting cannula is positioned in the interior bore of the guide member.

25. The follicular unit harvesting tool of claim 24, wherein the guide member axial passageway having an inner diameter sufficiently close to an outer diameter of the harvesting cannula so that tissue extending outwardly from the cannula distal end is displaced inwardly as the cannula distal end is withdrawn from the interior bore into the axial passageway of the guide member.

26. The follicular unit harvesting tool of claim 24, wherein the distal facing end of the guide member configured to dislodge from the grasper arm tips any tissue extending from a follicular unit carried in the harvesting cannula as the grasper device is moved from the closed position to the open position while initially mated to the guide member.

27. The follicular unit harvesting tool of claim 23, wherein the lumen of the harvesting cannula is in communication with a vacuum source such that the follicular unit is drawn into the lumen of the harvesting cannula by a pulling force of the vacuum source.

28. The follicular unit harvesting tool of claim 23, wherein the harvesting cannula lumen comprises a textured inner lumen wall.

29. The follicular unit harvesting tool of claim 23, wherein the tips comprise a bio-compatible material selected from the group comprising a metal, a hard plastic, stainless steel, polycarbonate, Teflon, silicone and rubber.

30. The follicular unit harvesting tool of claim 23, further comprising one or more of a mechanical system, electromechanical system, pneumatic system, hydraulic system or a magnetic system for effecting movement of the harvesting cannula and/or grasping device relative to one another.

31. The follicular unit harvesting tool of claim 23, wherein the harvesting tool is part of a robotic system, the robotic system comprising a robotic arm and a processor configured to maneuver the robotic arm to automatically position the harvesting tool.

32. The follicular unit harvesting tool of claim 23, wherein the tool is configured to be operatively connected to a robotic arm.

33. The follicular unit harvesting tool of claim 23, further including at least one camera operatively connected to the tool housing.

34. The follicular unit harvesting tool of claim 23, wherein the grasping device arm tips comprising respective opposing tissue engaging surfaces that mate when the grasping device is in the closed position.

35. The follicular unit harvesting tool of claim 23, at least one of the grasping device arm tips comprising an energy transmitting element configured to sever the connective tissue strand.

36. The follicular unit harvesting tool of claim 35, the energy transmitting element selected from the group comprising an electrode, an ultrasound transducer, and a laser.

37. The follicular unit harvesting tool of claim 23, further comprising a first fluid conduit coupled to first one of the grasping device arms, the first fluid conduit having an outlet for delivering fluid into a cavity when the grasping device is in the closed position.

38. The follicular unit harvesting tool of claim 37, further comprising a second fluid conduit coupled to a second one of the grasping device arms, the second fluid conduit having an outlet located in an inner wall of a respective tissue engaging surface groove of the second grasping arm tip for delivering fluid into the cavity when the grasping device is in the closed position.

39. The follicular unit harvesting tool of claim 23, the tissue grasping device comprising a first tissue grasping device, and further comprising a second tissue grasping device having two opposing arms extending to respective tissue engaging tips, at least one of the second tissue grasping device arm tips comprising an energy transmitting element configured to sever the connective tissue strand while the first tissue grasping device is in the closed position.

40. The follicular unit harvesting tool of claim 23, further comprising an actuation system operatively coupled to the grasping device and configured to provide controlled, synchronized movement of the grasping device arms from the open position to the closed position, and from the closed position to the open position, respectively.

41. The follicular unit harvesting tool of claim 23, further comprising an actuation system for effecting movement of the harvesting cannula and grasping device with respect to the tool housing and relative to one another, wherein the actuation system provides controlled lateral and longitudinal movement of the grasping device arms and allows the grasping device arms close after they have been extended longitudinally.

42. A follicular unit harvesting tool, comprising:

a tool housing;

a hair harvesting cannula extending from the tool housing, the hair harvesting cannula having an interior lumen sized for harvesting individual follicular units and an open distal end in communication with the lumen, the distal end having a coring edge configured to dissect tissue to encapsulate a follicular unit in the lumen of the harvesting cannula; and a grasping device extending from the tool housing and having two arms, each arm extending to a respective tip, one or both of the harvesting cannula and grasping device being movable with respect to the tool housing and relative to the other, the grasping device having an open position in which the arm tips are separated and a closed position in which the arm tips are positioned in close proximity to each other and beyond the distal end of the hair harvesting cannula, the grasping device being configured to grasp and/or sever a connective tissue strand connecting a follicular unit to a body surface from which the follicular unit was harvested;

wherein the tips of the arms of the grasping device comprise respective opposing tissue engaging surfaces and respective opposing grooves that together define a cavity shaped similar to and dimensioned to snugly seat therein the distal end of the hair harvesting cannula when the arms of the grasping device are in the closed position.

* * * * *